(12) United States Patent
Konstantinova et al.

(10) Patent No.: US 10,767,180 B2
(45) Date of Patent: *Sep. 8, 2020

(54) RNAI INDUCED HUNTINGTIN GENE SUPPRESSION

(71) Applicant: uniQure IP B.V., Amsterdam (NL)

(72) Inventors: Pavlina Stefanova Konstantinova, Amsterdam (NL); Jana Miniariková, Amsterdam (NL)

(73) Assignee: UNIQURE IP B.V., Amsterdam (NL)

(*) Notice: Subject to any disclaimer, the term of this patent is extended or adjusted under 35 U.S.C. 154(b) by 0 days.

This patent is subject to a terminal disclaimer.

(21) Appl. No.: 16/193,908

(22) Filed: Nov. 16, 2018

(65) Prior Publication Data

US 2019/0144860 A1  May 16, 2019

Related U.S. Application Data

(63) Continuation of application No. 15/538,964, filed as application No. PCT/EP2015/081157 on Dec. 23, 2015, now Pat. No. 10,174,321.

(30) Foreign Application Priority Data

Dec. 24, 2014 (EP) ..................... 14200308

(51) Int. Cl.
 *C12N 15/113* (2010.01)
 *A61K 31/713* (2006.01)

(52) U.S. Cl.
 CPC .......... *C12N 15/113* (2013.01); *A61K 31/713* (2013.01); *C12N 2310/14* (2013.01); *C12N 2310/141* (2013.01); *C12N 2310/3519* (2013.01); *C12N 2310/531* (2013.01); *C12N 2320/32* (2013.01); *C12N 2330/51* (2013.01)

(58) Field of Classification Search
 None
 See application file for complete search history.

(56) References Cited

U.S. PATENT DOCUMENTS

| | | | |
|---|---|---|---|
| 10,174,321 B2 * | 1/2019 | Konstantinova | A61K 31/713 |
| 2008/0015158 A1 | 1/2008 | Ichiro et al. | |
| 2009/0186410 A1 | 7/2009 | Aronin et al. | |
| 2011/0172291 A1 | 7/2011 | Aronin et al. | |

FOREIGN PATENT DOCUMENTS

| | | |
|---|---|---|
| WO | WO-2005/105995 A2 | 11/2005 |
| WO | WO-2008/134646 A2 | 11/2008 |
| WO | WO-2008/150897 A2 | 12/2008 |
| WO | WO-2011/133889 A2 | 10/2011 |

OTHER PUBLICATIONS

Boudreau et al., "Nonallele-specific silencing of mutant and wild-type huntingtin demonstrates therapeutic efficacy in Huntington's disease mice", Molecular Therapy, Feb. 2009, vol. 17, No. 6, pp. 1053-1063.
Franich et al., "AAV Vector-mediated RNAi of mutant huntingtin expression is neuroprotective in a novel genetic rat model of huntingtin's disease", Molecular Therapy, Mar. 2008, vol. 16, No. 5, pp. 947-956.
Mcbride et al., "Artificial miRNAs mitigate shRNA-mediated toxicity in the brain: Implication for the therapeutic development of RNAi", Proceedings of the National Academy of Sciences (PNAS), Apr. 15, 2008, vol. 105, No. 15, pp. 5868-5873.
Mcbride et al., "Preclinical safety of RNAi-mediated HTT suppression in the Rhesus Macaque as a potential therapy for Huntington's disease", Molecular Therapy, Dec. 2011, vol. 19, No. 2, pp. 2152-2162.
Rodriguez-Lebron et al., "Intrastriatal rAAV-mediated delivery iof anti-huntingtin shRNASs induces partial reversal of disease progression in R6/1 Huntington's disease transgenic mice", Molecular Therapy, Nature Publishing Group, Jul. 2005, vol. 12, No. 4, pp. 618-633.
International Search Report issued in International Patent Application No. PCT/EP2015/081157, dated Mar. 14, 2016.
Davidson et al., " Current prospects for RNA interference-based therapies", Nature Reviews—Genetics, May 2011, vol. 12, pp. 329-340.
Drouet et al., "Sustained effects of nonallele-specific Huntingtin silencing", Ann Neurol, 2009, vol. 65, pp. 276-285.

* cited by examiner

Primary Examiner — J. E Angell
(74) Attorney, Agent, or Firm — Foley & Lardner LLP; Sunit Talapatra

(57) ABSTRACT

The present invention provides for a double stranded RNA comprising a first RNA sequence and a second RNA sequence wherein the first and second RNA sequence are substantially complementary, wherein the first RNA sequence has a sequence length of at least 19 nucleotides and is substantially complementary to SEQ ID NO. 1. Said double stranded RNA is for use in inducing RNAi against Huntingtin exon 1 sequences. The double stranded RNA of to the invention was capable of reducing neuronal cell death and huntingtin aggregates in an animal model.

18 Claims, 20 Drawing Sheets
Specification includes a Sequence Listing.

Fig. 2A miH12_155

```
       1                                 26
5'- u g  c a u  c a  u  c c u g a a g g u u  u  c
   u g  g u g  g u  a  g g a c u u c c a a g  g  a
3'- a g  g a c  g u  a  c u g a a g g u u c c  a  c
    69                                    46
``` miH12_451a

```
        1                      17                              37
5'- c  u u g g g  a  g g  c a  u g g a c u u c u g a c c g g g a  a
    g  a c c c u  a  u c  g u  a c c u g a a g a c u g g c c c u  a
3'- a  g a c c a  a  u c  u c                                  a
    72                            56                           38
```

Figure 2C (SEQ ID NO.17)

**GTTGACATTGATTATTGACTAGTTATTAATAGTAATCAATTACGGGGT
CATTAGTTCATAGCCCATATATGGAGTTCCGCGTTACATAACTTACGG
TAAATGGCCCGCCTGGCTGACCGCCCAACGACCCCGCCCATTGACGT
CAATAATGACGTATGTTCCCATAGTAACGCCAATAGGGACTTTCCATT
GACGTCAATGGGTGGAGTATTTACGGTAAACTGCCCACTTGGCAGTAC
ATCAAGTGTATCATATGCCAAGTACGCCCCTATTGACGTCAATGACG
GTAAATGGCCCGCCTGGCATTATGCCCAGTACATGACCTTATGGGACT
TTCCTACTTGGCAGTACATCTACGTATTAGTCATCGCTATTACCATGG
TGATGCGGTTTTGGCAGTACATCAATGGGCGTGGATAGCGGTTTGACT
CACGGGGATTTCCAAGTCTCCACCCCATTGACGTCAATGGGAGTTTGT
TTTGGCACCAAAATCAACGGGACTTTCCAAAATGTCGTAACAACTCCG
CCCCATTGACGCAAATGGGCGGTAGGCGTGTACGGTGGGAGGTCTATA
TAAGCAGAGCTC**TCTGGCTAACTAGAGAACCCACTGCTTACTGGCTTA
TCGAAATTAATACGACTCACTATAGGGAGTCCCAAGCTGGCTAGTTAA
GCTATCAACAAGTTTGTACAAAAAGCAGGCTTTAAAACC*ATGGTGAG*
*CAAGGGCGAGGAGCTGTTCACCGGGGTGGTGCCCATCCTGGTCGAGCT*
*GGACGGCGACGTAAACGGCCACAAGTTCAGCGTGTCCGGCGAGGGCGA*
*GGGCGATGCCACCTACGGCAAGCTGACCCTGAAGTTCATCTGCACCAC*
*CGGCAAGCTGCCCGTGCCCTGGCCCACCCTCGTGACCACCTTCACCTA*
*CGGCGTGCAGTGCTTCGCCCGCTACCCCGACCACATGAAGCAGCACGA*
*CTTCTTCAAGTCCGCCATGCCCGAAGGCTACGTCCAGGAGCGCACCAT*
*CTTCTTCAAGGACGACGGCAACTACAAGACCCGCGCCGAGGTGAAGTT*
*CGAGGGCGACACCCTGGTGAACCGCATCGAGCTGAAGGGCATCGACTT*
*CAAGGAGGACGGCAACATCCTGGGGCACAAGCTGGAGTACAACTACAA*
*CAGCCACAAGGTCTATATCACCGCCGACAAGCAGAAGAACGGCATCAA*
*GGTGAACTTCAAGACCCGCCACAACATCGAGGACGGCAGCGTGCAGCT*
*CGCCGACCACTACCAGCAGAACACCCCCATCGGCGACGGCCCCGTGCT*
*GCTGCCCGACAACCACTACCTGAGCACCCAGTCCGCCCTGAGCAAAGA*
*CCCCAACGAGAAGCGCGATCACATGGTCCTGCTGGAGTTCGTGACCGC*

Figure 2C continued

*CGCCGGGATCACTCTCGGCATGGACGAGCTGTACAAGTAA*GCTAAGCA
CTTCGTGGCCGTCGATCGTTTAAAGGGAGGTAGTGAGTCGACCAGTGG
ATCCTGGAGGCTTGCTGAAGGCTGTATGCTGAAGGACTTGAGGGACTC
GAAGGTTTTGGCCACTGACTGAC*CTTCGAGTCTCAAGTCCTT*CAGGAC
ACAAGGCCTGTTACTAGCACTCACATGGAACAAATGGCCCAGATCTGG
CCGCACTCGAGATATCTAGACCCAGCTTTCTTGTACAAAGTGGTTGAT
CTAGAGGGCCCGCGGTTCGCTGATGGGGGAGGCTAACTGAAACACGGA
AGGAGACAATACCGGAAGGAACCCGCGCTATGACGGCAATAAAAAGAC
AGAATAAAACGCACGGGTGTTGGGTCGTTTGTTCATAAACGCGGGGTT
CGGTCCCAGGGCTGGCACTCTGTCGATACCCCACCGTGACCCCATTGG
GGCCAATACGCCCGCGTTTCTTCCTTTTCCCCACCCCACCCCCAAGT
TCGGGTGAAGGCCCAGGGCTCGCAGCCAACGTCGGGGCGGCAGGCCCT
GCCATAGCATCCCCTATAGTG

Fig.2 D (SED ID NO.18)

CAGTCACGACGTTGTAAAACGACGGCCAGTGAATTCGCCCTT**AATTCG
GTACCCTAGTTATTAATAGTAATCAATTACGGGGTCATTAGTTCATAG
CCCATATATGGAGTTCCGCGTTACATAACTTACGGTAAATGGCCCGCC
TGGCTGACCGCCCAACGACCCCGCCCATTGACGTCAATAATGACGTA
TGTTCCCATAGTAACGCCAATAGGGACTTTCCATTGACGTCAATGGGT
GGACTATTTACGGTAAACTGCCCACTTGGCAGTACATCAAGTGTATCA
TATGCCAAGTACGCCCCTATTGACGTCAATGACGGTAAATGGCCCGC
CTGGCATTATGCCCAGTACATGACCTTATGGGACTTTCCTACTTGGCA
GTACATCTACGTATTAGTCATCGCTATTACCATGGTCGAGGTGAGCCC
CACGTTCTGCTTCACTCTCCCCATCTCCCCCCCTCCCCACCCCCAAT
TTTGTATTTATTTATTTTTTAATTATTTTGTGCAGCGATGGGGGCGGG
GGGGGGGGGGGGGCGCGCGCCAGGCGGGGCGGGGCGGGGCGAGGGGCG
GGGCGGGGCGAGGCGGAGAGGTGCGGCGGCAGCCAATCAGAGCGGCGC
GCTCCGAAAGTTTCCTTTTATGGCGAGGCGGCGGCGGCGGCGGCCCTA
TAAAAGCGAAGCGCGCGGCGGGCGGGAGTCGCTGCGACGCTGCCTTC
GCCCCGTGCCCCGCTCCGCCGCCGCCTCGCGCCGCCCGCCCCGGCTCT
GACTGACCGCGTTACTCCCACAAGTGAGCGGGCGGGACGGCCCTTCTC
CTCCGGGCTGTAATTAGCGCTTGGTTTAATGACGGCTTGTTTCTTTTC
TGTGGCTGCGTGAAAGCCTTGAGGGGCTCCGGGAGGGCCCTTTGTGCG
GGGGGGAGCGGCTCGGGGGGTGCGTGCGTGTGTGTGCGTGGGGAGC
GCCGCGTGCGGCCCGCGCTGCCCGGCGGCTGTGAGCGCTGCGGGCGCG
GCGCGGGGCTTTGTGCGCTCCGCAGTGTGCGCGAGGGGAGCGCGGCCG
GGGGCGGTGCCCGCGGTGCGGGGGGGCTGCGAGGGGAACAAAGGCT
GCGTGCGGGGTGTGTGCGTGGGGGGGTGAGCAGGGGGTGTGGGCGCGG
CGGTCGGGCTGTAACCCCCCCTGCACCCCCCTCCCCGAGTTGCTGAG
CACGGCCCGGCTTCGGGTGCGGGCTCCGTACGGGCGTGGCGCGGGG
CTCGCCGTGCCGGGCGGGGGGTGGCGGCAGGTGGGGTGCCGGGCGGG
GCGGGGCCGCCTCGGGCCGGGGAGGGCTCGGGGGAGGGGCGCGGCGGC
CCCCGGAGCGCCGGCGGCTGTCGAGGCGCGGCGCGCCGCAGCCATTGC**

Fig.2 D continued

CTTTTATGGTAATCGTGCGAGAGGGCGCAGGGACTTCCTTTGTCCCAA
ATCTGTGCGGAGCCGAAATCTGGGAGGCGCCGCCGCACCCCCTCTAGC
GGGCGCGGGGCGAAGCGGTGCGGCGCCGGCAGGAAGGAAATGGGCGGG
GAGGGCCTTCGTGCGTCGCCGCCGCCGTCCCCTTCTCCCTCTCCAG
CCTCGGGGCTGTCCGCGGGGGGACGGCTGCCTTCGGGGGGGACGGGGC
AGGGCGGGGTTCGGCTTCTGGCGTGTGACCGGCGGCTCTAGAGCCTCT
GCTAACCATGTTCATGCCTTCTTCTTTTTCCTACAGCTCCTGGGCAAC
GTGCTGGTTATTGTGCTGTCTCATCATTTTGGCAAAGAATTAAGGGCG
AATTCGAGCTCGGTACCTCGCGAATGCATCTAGATATCGGCGCTATGC
TTCCTGTGCCCCAGTGGGGCCCTGGCTGGATTTCATCATATACTGT
AAGTTTGCGATGAGACACTACAGTATAGATGATGTACTAGTCCGGCA
CCCCCAGCTCTGGAGCCTGACAAGGAGGACAGGAGAGATGCTGCAAGC
CCAAGAAGCTCTCTGCTCAGCCTGTCACAACCTACTGACTGCCAGGGC
ACTTGGGAATGGCAAGG*AAGGACTTGAGGGACTCGAAGACGAGTCCCT*
*CAAGTCCTC*TCTTGCTATACCCAGAAAACGTGCCAGGAAGAGAACTCA
GGACCCTGAAGCAGACTACTGGAAGGGAGACTCCAGCTCAAACAAGGC
AGGGGTGGGGCGTGGGATTGGGGGTAGGGGAGGGAATAGATACATTT
TCTCTTTCCTGTTGTAAAGAAATAAAGATAAGCCAGGCACAGTGGCTC
ACGCCTGTAATCCCACCACTTTCAGAGGCCAAGGCGCTGGATCCAGAT
CTCGAGCGGCCGCCCGTGGCATCCTGTGACCCCTCCCCAGTGCCTCT
CCTGGCCCTGGAAGTTGCCACTCCAGTGCCCACCAGCCTTGTCCTAAT
AAAATTAAGTTGCATCAAGATCGACGGGCCCGTCGACTGCAGAG

Fig. 2E (SEQ ID NO.19)

GTTGTAAAACGACGGCCAGTGAATTCTACCGGGTAGGGGAGGCGCTTT
TCCCAAGGCAGTCTGGAGCATGCGCTTTAGCAGCCCCGCTGGGCACTT
GGCGCTACACAAGTGGCCTCTGGCCTCGCACACATTCCACATCCACCG
GTAGGCGCCAACCGGCTCCGTTCTTTGGTGGCCCCTTCGCGCCACCTT
CTACTCCTCCCCTAGTCAGGAAGTTCCCCCCGCCCCGCAGCTCGCGT
CGTGCAGGACGTGACAAATGGAAGTAGCACGTCTCACTAGTCTCGTGC
AGATGGACAGCACCGCTGAGCAATGGAAGCGGGTAGGCCTTTGGGGCA
GCGGCCAATAGCAGCTTTGCTCCTTCGCTTTCTGGGCTCAGAGGCTGG
GAAGGGGTGGGTCCGGGGCGGGCTCAGGGGCGGGCTCAGGGGCGGGG
CGGGCGCCCGAAGGTCCTCCGGAGGCCCGGCATTCTGCACGCTTCAAA
AGCGCACGTCTGCCGCGCTGTTCTCCTCTTCCTCATCTCCGGGCCTTT
CGACCCGGATCCCCGGGCTGCAGGAATTCGAGCTCGGTACCTCGCGA
ATGCATCTAGATATCGGCGCTATGCTTCCTGTGCCCCAGTGGGGCCC
TGGCTGGATTTCATCATATACTGTAAGTTTGCGATGAGACACTACAG
TATAGATGATGTACTAGTCCGGGCACCCCAGCTCTGGAGCCTGACAA
GGAGGACAGGAGAGATGCTGCAAGCCCAAGAAGCTCTCTGCTCAGCCT
GTCACAACCTACTGACTGCCAGGGCACTTGGGAATGGCAAGG<u>*AAGGAC*</u>
<u>*TTGAGGGACTCGAAG*ACGAGTCCCTCAAGTCCTCTCTTGCTATACCCA</u>
<u>GAAAACGTGCCAGGAAGAGAACTCAGGACCCTGAAGCAGACTACTGGA</u>
AGGGAGACTCCAGCTCAAACAAGGCAGGGTGGGGGCGTGGGATTGGG
GGTAGGGGAGGGAATAGATACATTTCTCTTTCCTGTTGTAAAGAAAT
AAAGATAAGCCAGGCACAGTGGCTCACGCCTGTAATCCCACCACTTTC
AGAGGCCAAGGCGCTGGATCCAGATCTCGAGCGGCCGCCCGTGGCATC
CCTGTGACCCCTCCCCAGTGCCTCTCCTGGCCCTGGAAGTTGCCACTC
CAGTGCCCACCAGCCTTGTCCTAATAAAATTAAGTTGCATCAAGATCG
ACGGGCCCGTCGACTGCAGAGGCC

Fig. 2F - pri-miH12-155 (SEQ ID NO.20)

GCUAAGCACUUCGUGGCCGUCGAUCGUUUAAAGGGAGGUAGUGAGUCG
ACCAGUGGAUCCUGGAGGCUUGCUGAAGGCUGUAUGCUGAAGGACUUG
AGGGACUCGAAGGUUUUGGCCACUGACUGAC*CUUCGAGUCUCAAGUCC*
*UU*CAGGACACAAGGCCUGUUACUAGCACUCACAUGGAACAAAUGGCCC
AGAUCGGCCGCACUCGAGAUAUCUAGACCCAGCUUUCUUGUACAAAG
UGGUUGAUCUAGAGGGCCCGCGGUUCGCUGAU

Fig. 2G - pri-miH12-451 (CAG construct, SEQ ID NO.21)

GCUCCUGGGCAACGUGCUGGUUAUUGUGCUGUCUCAUCAUUUUGGCAA
AGAAUUAAGGGCGAAUUCGAGCUCGGUACCUCGCGAAUGCAUCUAGAU
AUCGGCGCUAUGCUUCCUGUGCCCCAGUGGGGCCCUGGCUGGGAUUU
CAUCAUAUACUGUAAGUUUGCGAUGAGACACUACAGUAUAGAUGAUGU
ACUAGUCCGGGCACCCCAGCUCUGGAGCCUGACAAGGAGGACAGGAG
AGAUGCUGCAAGCCCAAGAAGCUCUCUGCUCAGCCUGUCACAACCUAC
UGACUGCCAGGGCACUUGGGAAUGGCAAGGAAGGACUUGAGGGACUCG
AAGACGAGUCCCUCAAGUCCUCUCUUGCUAUACCCAGAAAACGUGCCA
GGAAGAGAACUCAGGACCCUGAAGCAGACUACUGGAAGGGAGACUCCA
GCUCAAACAAGGCAGGGGUGGGGGCGUGGGAUUGGGGGUAGGGGAGGG
AAUAGAUACAUUUCUCUUUCCUGUUGUAAAGAAAUAAAGAUAAGCCA
GGCACAGUGGCUCACGCCUGUAAUCCCACCACUUUCAGAGGCCAAGGC
GCUGGAUCCAGAUCUCGAGCGGCCGCCCG

Fig. 2H - pri-miH12-451

(PGK construct, SEQ ID NO.22)

AGUCUCGUGCAGAUGGACAGCACCGCUGAGCAAUGGAAGCGGGUAGGC
CUUUGGGGCAGCGGCCAAUAGCAGCUUUGCUCCUUCGCUUUCUGGGCU
CAGAGGCUGGGAAGGGGUGGGUCCGGGGGCGGGCUCAGGGGCGGGCUC
AGGGGCGGGGCGGGCGCCCGAAGGUCCUCCGGAGGCCCGGCAUUCUGC
ACGCUUCAAAAGCGCACGUCUGCCGCGCUGUUCUCCUCUUCCUCAUCU
CCGGGCCUUUCGACCCGGAUCCCCGGGCUGCAGGAAUUCGAGCUCGG
UACCUCGCGAAUGCAUCUAGAUAUCGGCGCUAUGCUUCCUGUGCCCCC
AGUGGGGCCCUGGCUGGGAUUUCAUCAUAUACUGUAAGUUUGCGAUGA
GACACUACAGUAUAGAUGAUGUACUAGUCCGGGCACCCCCAGCUCUGG
AGCCUGACAAGGAGGACAGGAGAGAUGCUGCAAGCCCAAGAAGCUCUC
UGCUCAGCCUGUCACAACCUACUGACUGCCAGGGCACUUGGGAAUGGC
AAGG*AAGGACUUGAGGGACUCGAAG*ACGAGUCCCUCAAGUCCUCUCUU
GCUAUACCCAGAAAACGUGCCAGGAAGAGAACUCAGGACCCUGAAGCA
GACUACUGGAAGGGAGACUCCAGCUCAAACAAGGCAGGGGUGGGGGCG
UGGGAUUGGGGGUAGGGGAGGGAAUAGAUACAUUUCUCUUUCCUGUU
GUAAAGAAAUAAAGAUAAGCCAGGCACAGUGGCUCACGCCUGUAAUCC
CACCACUUUCAGAGGCCAAGGCGCUGGAUCCAGAUCUCGAGCGGCCGC
CCG

RNAI INDUCED HUNTINGTIN GENE SUPPRESSION

CROSS-REFERENCE TO RELATED APPLICATIONS

This application is a Continuation of U.S. application Ser. No. 15/538,964, filed Jun. 22, 2017, which is the National Phase of International Patent Application No. PCT/EP2015/081157, filed Dec. 23, 2015, published on Jun. 30, 2016 as WO 2016/102664 A1, which claims priority to European Patent Application No. 14200308.6, filed Dec. 24, 2014. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Jun. 22, 2017, is named 100607-0300SequenceListing.txt and is 20 KB.

BACKGROUND

The huntingtin gene, also referred to as the HTT or HD (Huntington's disease) gene, encodes for the huntingtin protein. The huntingtin gene is a large gene of about 13.5 kb (huntingtin protein is about 350 kDa). Huntington's disease is a genetic neurodegenerative disorder caused by a genetic mutation in the huntingtin gene. The genetic mutation involves a DNA segment of the huntingtin gene known as the CAG trinucleotide repeat. Normally, the CAG segment in the huntingtin gene of humans is repeated multiple times, i.e. about 10-35 times. People that develop Huntington's disease have an expansion of the number of CAG repeats in at least one allele. An affected person usually inherits the mutated allele from one affected parent. In rare cases, an individual with Huntington's disease does not have a parent with the disorder (sporadic HD). People with 36 to 39 CAG repeats may develop signs and symptoms of Huntington disease, while people with 40 or more repeats almost always develop the disorder. The increase in the size of the CAG repeat leads to the production of an elongated (mutated) huntingtin protein. This protein is processed in the cell into smaller fragments that are cytotoxic and that accumulate and aggregate in neurons. This results in the disruption of normal function and eventual death of neurons. This is the process that occurs in the brain which underlies the signs and symptoms of Huntington's disease.

RNA interference (RNAi) is a naturally occurring mechanism that involves sequence specific down regulation of mRNA. The down regulation of mRNA results in a reduction of the amount of protein that is expressed. RNA interference is triggered by double stranded RNA. One of the strands of the double stranded RNA is substantially or completely complementary to its target, the mRNA. This strand is termed the guide strand. The mechanism of RNA interference involves the incorporation of the guide strand in the RNA-induced silencing complex (RISC). This complex is a multiple turnover complex that via complementary base paring binds to its target mRNA. Once bound to its target mRNA it can either cleave the mRNA or reduce translation efficiency. RNA interference has since its discovery been widely used to knock down specific target genes. The triggers for inducing RNA interference that have been employed involve the use of siRNAs or shRNAs. In addition, molecules that can naturally trigger RNAi, the so called miRNAs, have been used to make artificial miRNAs that mimic their naturally occurring counterparts. These strategies have in common that they provide for substantially double stranded RNA molecules that are designed to target a gene of choice. RNAi based therapeutic approaches that utilise the sequence specific modality of RNAi are under development and several are currently in clinical trials (see i.a. Davidson and McCray, Nature Reviews—Genetics, 2011; Vol. 12; 329-340).

As Huntington's disease involves the expression of a mutant huntingtin protein, the accumulation thereof leading to disease, RNA interference provides for an opportunity to treat the disease as it can reduce expression of the huntingtin gene. The paradigm underlying this approach involves a reduction of the mutant Htt protein to thereby reduce the toxic effects resulting from the mutant Htt protein to achieve a reduction and/or delay of Huntington's disease symptoms, or even to prevent Huntington's disease symptoms altogether. Targeting huntingtin gene suppression has been hypothesized in the prior art, including the listing of about two thousand of hypothetical siRNA target sequences (WO2005105995). Strategies to reduce huntingtin gene expression are known in the art and involve the specific targeting of mutant huntingtin genes (e.g. US20090186410, US20110172291). Alternatively, RNA interference has also been employed to target both mutant and non-mutant genes (e.g. Rodriguez-Lebron et al., 2005, Mol Ther. Vol 12 No. 4: 618-633; Franich et al., 2008, Mol Ther, Vol. 16 No. 5; 947-956; Drouet et al., 2009, Annals of Neurology; Vol. 65 No. 3; 276-285 and McBride et al. Mol Ther. 2011 December; 19(12):2152-62; US20080015158, WO2008134646). In the latter case, knockdown of the wild type Huntingtin protein was shown not to have any apparent detrimental effects.

SUMMARY OF THE INVENTION

The present invention provides for a double stranded RNA comprising a first RNA sequence and a second RNA sequence wherein the first and second RNA sequence are substantially complementary, wherein the first RNA sequence has a sequence length of at least 19 nucleotides and is substantially complementary to SEQ ID NO. 1. A large number of target sequences were tested for effective knockdown of the huntingtin gene. The selected double stranded RNA of the current invention was found to be effective in reducing huntingtin gene expression. Said double stranded RNA when provided in a cell, either directly via transfection or indirectly via delivery of DNA (e.g. transfection) or via vector-mediated expression upon which the said double stranded RNA can be expressed, is capable of reducing expression of both a mutated huntingtin gene and a normal huntingtin gene. Furthermore, it was shown that the double stranded RNA of the invention was capable of reducing target gene expression when provided either as an siRNA or in a miRNA scaffold. When tested in an animal model, it was shown that a double stranded RNA according to the invention was capable of reducing neuronal cell death and huntingtin aggregates. The double stranded RNA as provided in the current invention provides for an improvement as compared to double stranded RNAs in the art targeting the huntingtin gene, or provides for at least an alternative thereto.

The double stranded RNA according to the invention can be provided as an siRNA, a shRNA, a pre-miRNA or pri-miRNA. Such double stranded RNAs may be delivered to the target cells directly, e.g. via cellular uptake using e.g. transfection methods. Preferably, said delivery is achieved using a gene therapy vector, wherein an expression cassette for the siRNA, shRNA, pre-miRNA or pri-miRNA is included in a vector. This way, cells can be provided with a constant supply of double stranded RNA to achieve durable huntingtin gene suppression without requiring repeated administration. Preferably, the viral vector of choice is AAV5. The current invention thus also provides for the medical use of a double stranded RNA according to the invention, such as the treatment or Huntington's disease, wherein such medical use may also comprise an expression cassette or a viral vector, such as AAV5, capable of expressing the said double stranded RNA of the invention.

BRIEF DESCRIPTION OF THE FIGURES

FIGS. 2A-2H. Examples of double stranded RNAs and expression cassettes. (A) Examples of pri-/pre-miRNA scaffold for miH12 pre-miH12-155 (SEQ ID NO. 44) and pre-miH12-451 scaffold (SEQ ID NO. 45) with miH12 guide (grey) indicated. (B) Schematic outlining of the double stranded RNAs in accordance with the invention and how they can be processed by the RNAi machinery. A double stranded RNA may be a short hairpin RNA (1) or an extended siRNA (2). The hairpin RNA or extended siRNA has the first RNA sequence at the proximal end, as indicated (indicated with 1 and brackets). A short hairpin RNA or an extended siRNA can be processed by the RNAi machinery in the cell to produce an siRNA (3), which can also be a double stranded RNA according to the invention, of which one strand comprising the first RNA sequence can be incorporated into the RISC complex (4). A double stranded RNA can be comprised in a pri-miRNA sequence (5) or a pre-miRNA sequence (6). The pri-miRNA can be processed by the RNAi machinery to produce a pre-miRNA and subsequently a mature miRNA duplex (7), of which one strand comprising the first RNA sequence can be incorporated into the RISC complex (4). The position of the first RNA sequence in the pre-miRNA, pri-miRNA and miRNA duplex is indicated 1 and brackets. (C) DNA sequence of the pVD-CMV-miH12-155 expression cassette (CMV promoter (1-588), intervening sequence, Green Fluorescent Protein GFP sequence (713-1432), 5' pri-miRNA flank (1433-1514), 5' pre-miRNA, Guide strand (first RNA sequence) (1520-1540), loop sequence, Passenger strand (second RNA sequence) (1560-1578), 3' pre-miRNA) 3' pri-miRNA flank (1584-1704), HSV TKpolyA signal (1705-1976); (D) DNA sequence of the pVD-CAG-miH12-451 (CAG promoter (43-1715), 5' pri-miRNA flank (1716-2017), 5' pre-miRNA, Guide strand (first RNA sequence) (2034-2054), second RNA sequence &, 3' pre-miRNA, 3' pri-miRNA flank (2090-2320), hGH polyA signal (2321-2417) and (E) DNA sequence of the pVD-PGK-miH12-451 expression cassette (PGK promoter (23-277), 5' pri-miRNA flank (278-794), 5' pre-miRNA, Guide strand (first RNA sequence) (811-831), second RNA sequence &, 3' pre-miRNA, 3' pri-miRNA flank (867-1097), hGH polyA signal (1098-1194). (F) pri-miH12-155 sequence that is encoded by pVD-CMV-miH12-155. (G) pri-miH12-451 sequence that is encoded by pVD-CAG-miH12-451. (G) pri-miH12-451 sequence that is encoded by pVD-PGK-miH12-451. For figure (E), (F) and (G), the font type is the same as used above for the corresponding DNA. Promoter sequences are bold, Green Fluorescent protein sequence is in italics underlined (only C), pri-miRNA sequences have a normal font type, guide strand (first RNA sequence) is in bold italics and the passenger strand or second RNA sequence is in italics, pre-miRNA sequences are underlined and the polyA signal is bold underlined.

(B) LucHTT knockdown was by synthetic siH12 with 19-23 nucleotides of length.

Figure 3A:
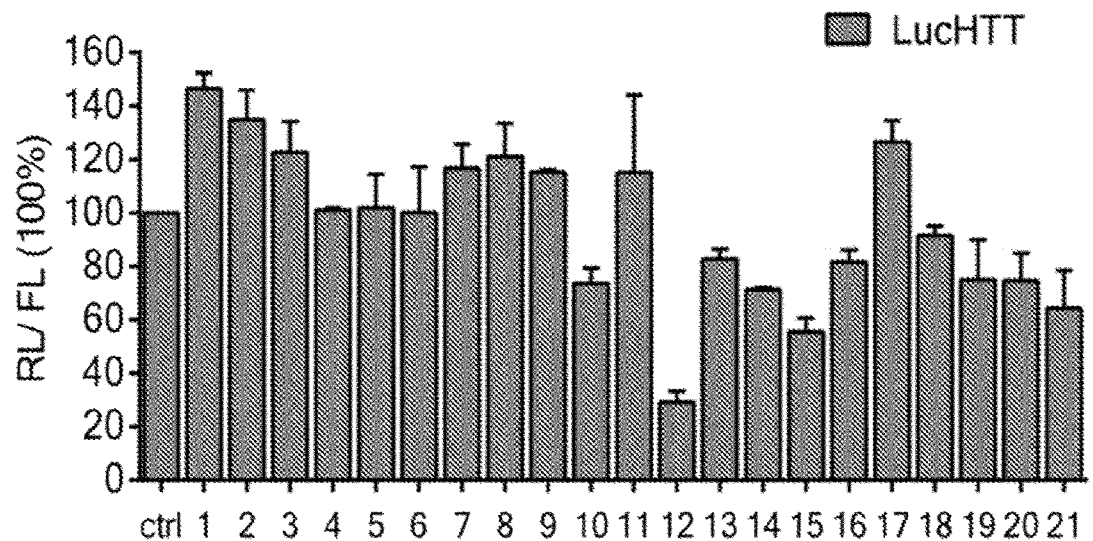
FIGS. 3A and 3B. In vitro knockdown efficacy of miH1-21. (A) Total HTT knockdown by targeting exon 1. LucHTT was co-transfected in Hek293T cells with miH1-miH21. *Renilla* and Firefly luciferase fluorescence was measured 48 h post-transfection. miScr (ctrl) was used as a negative control and was set at 100%. miH12 showed strongest knockdown efficiency.
Figure 3B:
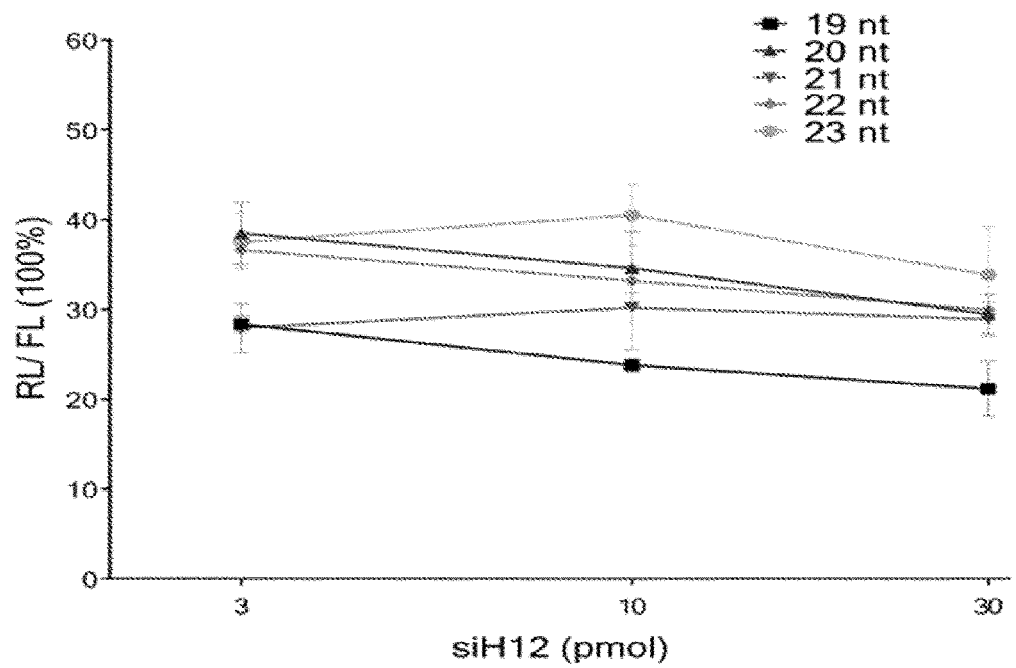
Figure 4A:
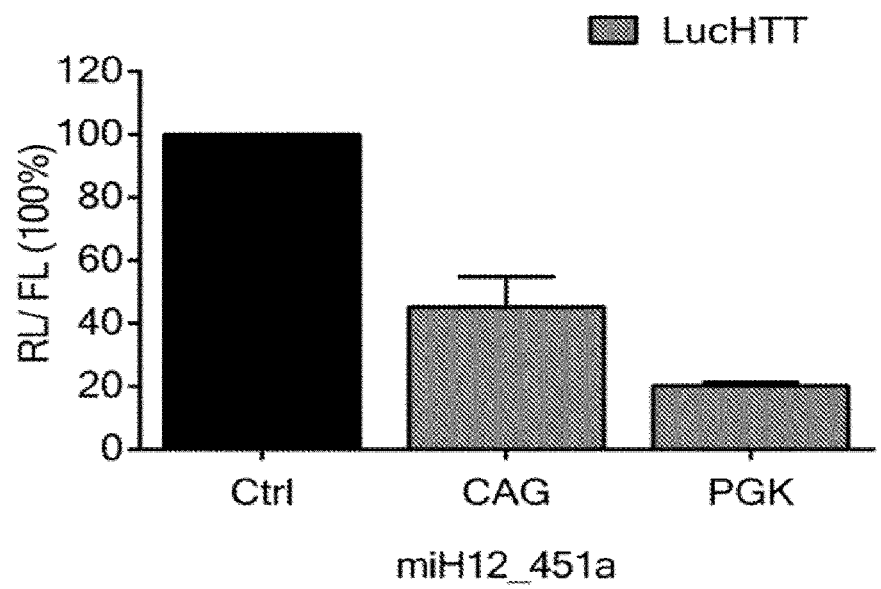
Figure 4B:
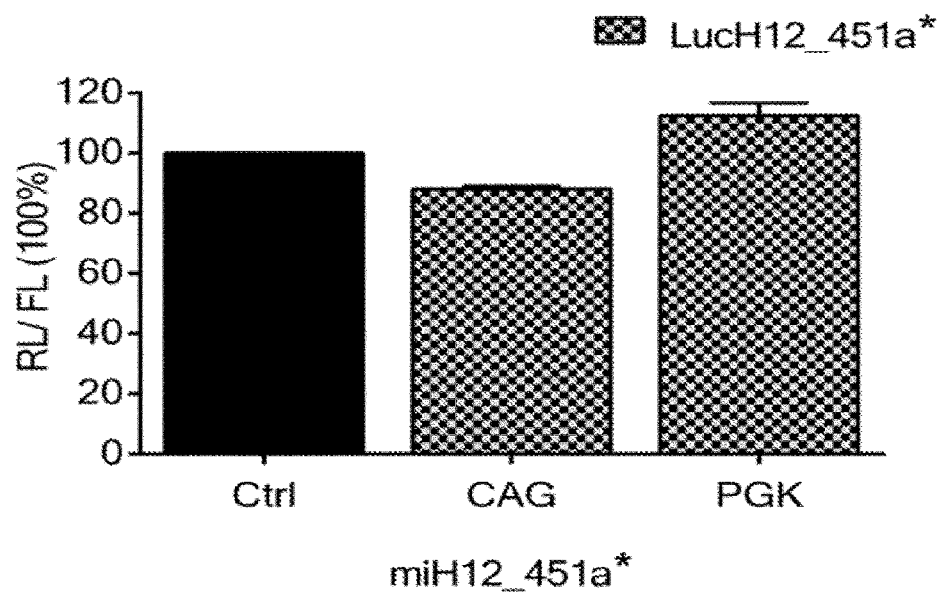

FIGS. 4A and 4B. In vitro knockdown efficacy of miH12-451 with different promoters. (A) LucHTT reporter has been co-transfected with CAG-miH12 or PGK-miH12 variants and knockdown efficacy was determined as described above for FIG. 3. (B) Passenger (*) strand activity of miH12-451* expressed from the CAG or PGK promoters was measured on specific LucHTT* reporters. No passenger strand activity was detected.

Figure 5:
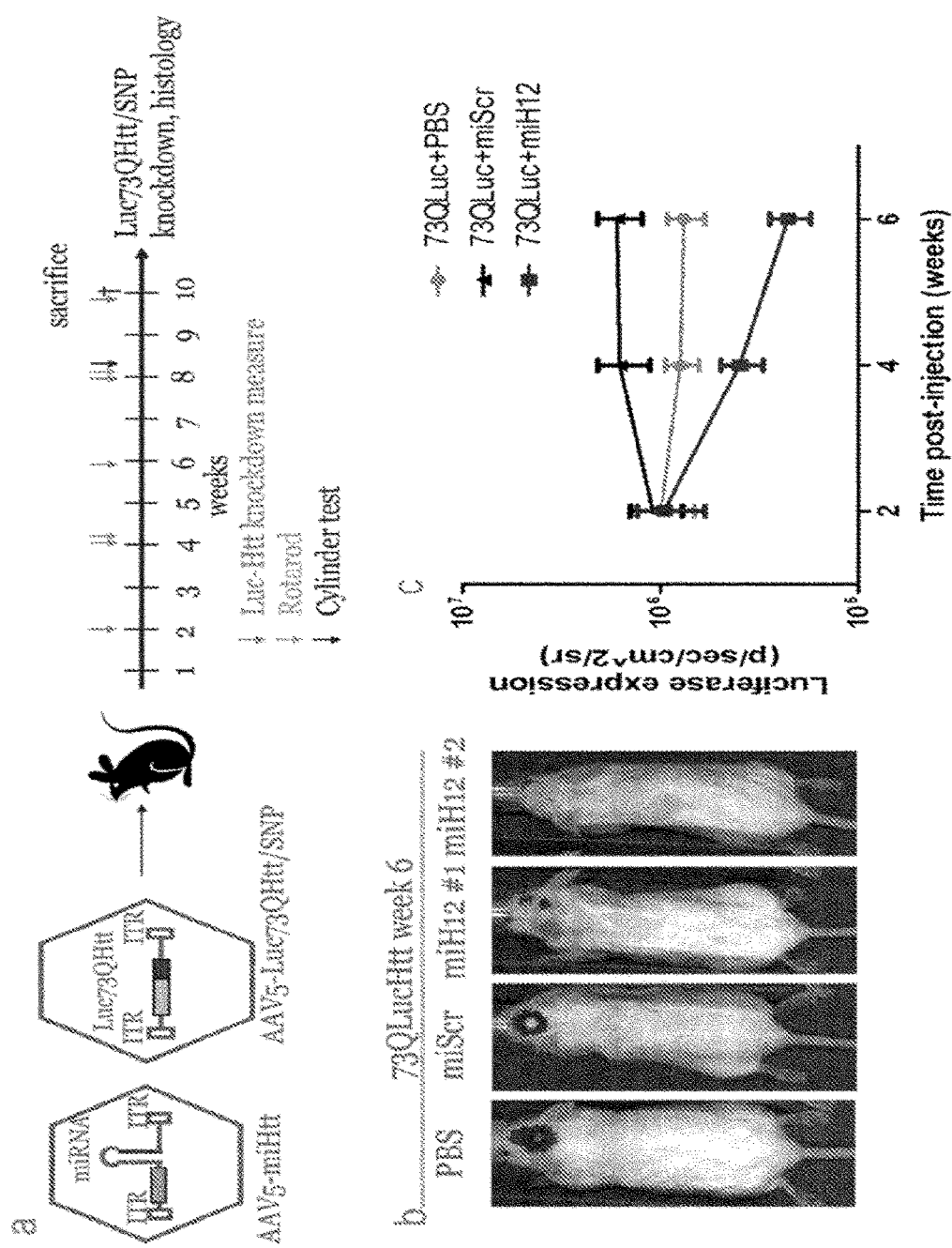

FIG. 5. In vivo efficacy of AAV5-delivered miH12. (A) Experimental set up. Mice were co-injected with AAV5-Luc73QHTT and AAV5-CMV-miScr-155 or AAV5-CMV-miH12-155 in 1:5 ratio. Measurement points are indicated with arrows; (B) AAV5-Luc73QHTT knockdown in animals 6 weeks p.i. was measured by IVIS; (C) AAV5-Luc73QHTT knockdown trend by AAV5-miH12 up to 6 weeks p.i.

FIGS. 6A-6D. Human HTT knockdown proof of concept in rat HD mechanistic model. (A) Experimental set up; (B) brain histology showing less neurodegeneration (DARP32) and less mutant Htt (EM48) aggregates in the AAV5-CMV-miH12-155 group; (C) GFP brain histology; (D) Iba1 immune activation marker brain histology.

Figure 7A:
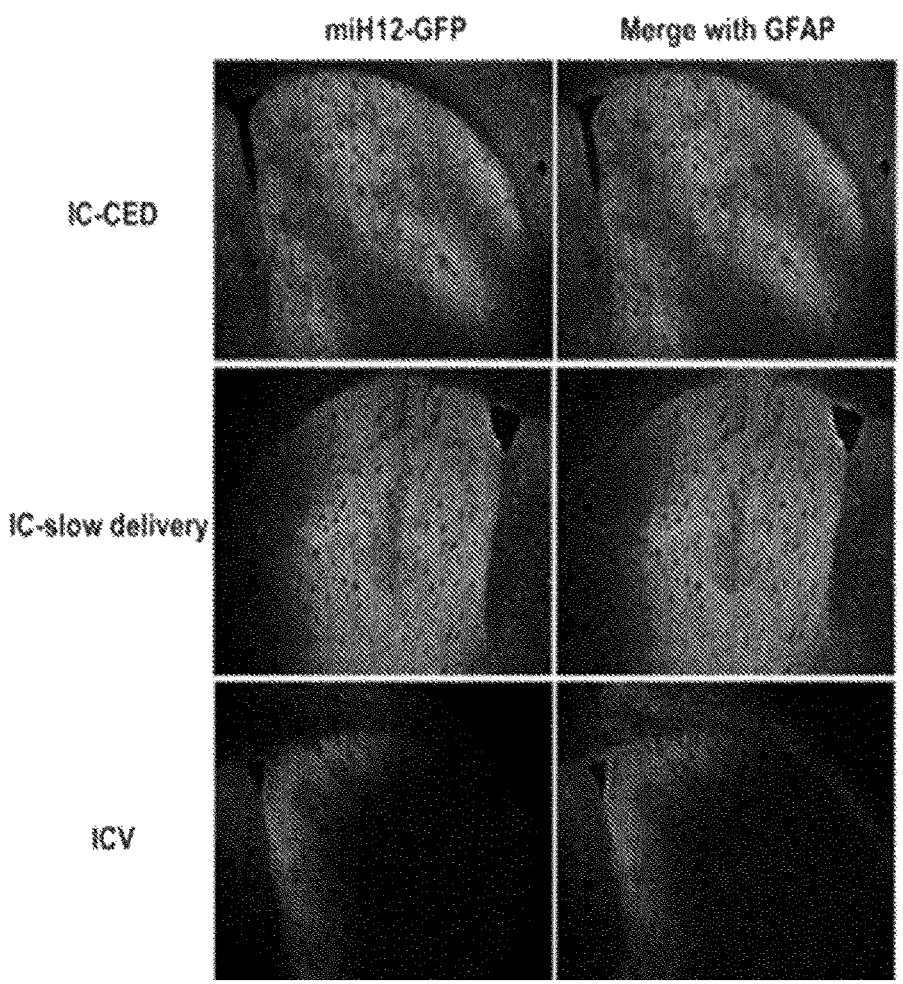
Figure 7B:
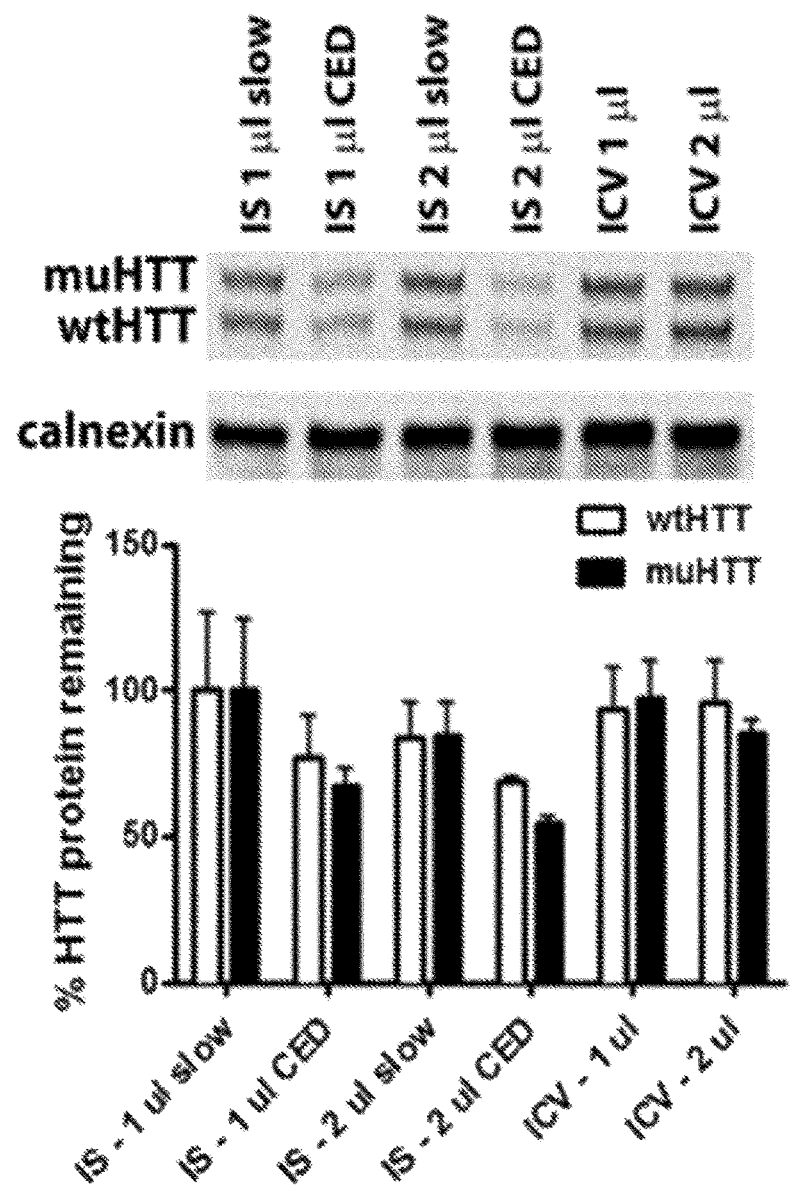

FIGS. 7A and 7B. Human HTT knockdown in the humanized Hu97/18 HD mouse model. (A) Transduction efficiency in murine brain upon slow intrastriatal injection, convection enhanced diffusion (CED) intrastriatal injection or intracerebral ventricular (ICV) injection of AAV5-CMV-miH12-155. GFP fluorescence was viewed 5 weeks post injection. (B) Western blot measuring human HTT knockdown in murine brain upon AAV5-miHTT delivery. (C) HTT western blot quantification.

Figure 8A:
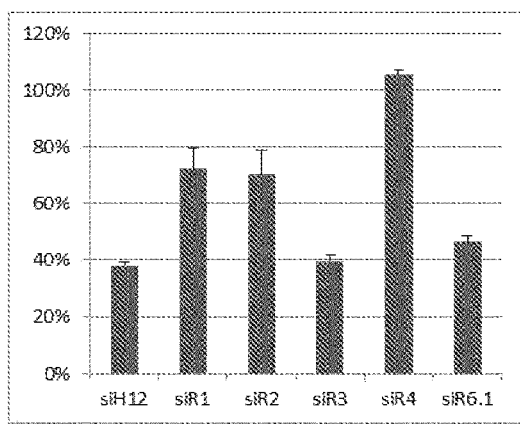
Figure 8B:
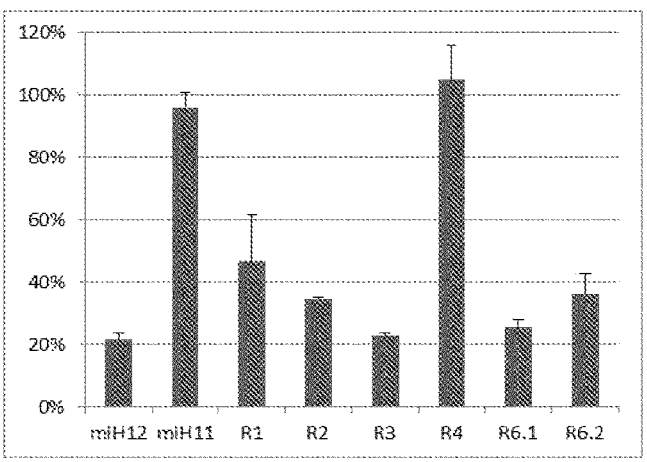
Figure 8C:
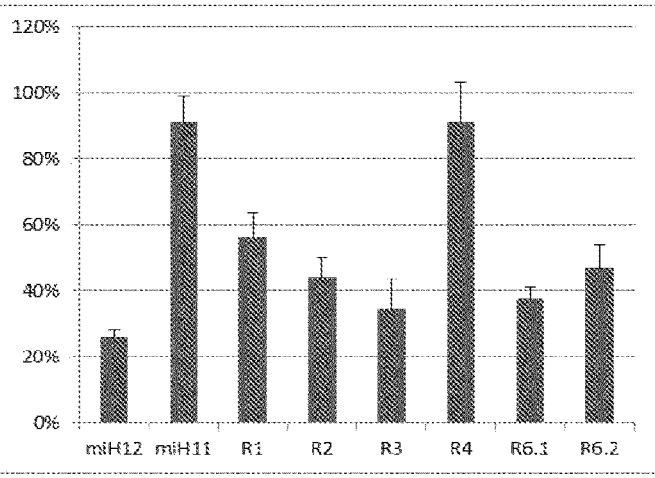

FIGS. 8A-8C. Comparison of selected H12 target with prior art target sequences. LucHTT was co-transfected in Hek293T cells with the indicated siRNAs (A) and miRNA constructs (B and C). *Renilla* and Firefly luciferase fluorescence was measured 48 h post-transfection. miH12 and siH12 showed strongest knockdown efficiency.

DETAILED DESCRIPTION

The present invention provides for a double stranded RNA comprising a first RNA sequence and a second RNA sequence wherein the first and second RNA sequence are substantially complementary, wherein the first RNA sequence has a sequence length of at least 19 nucleotides and is substantially complementary to SEQ ID NO. 1.

Figures 1A, 1B:
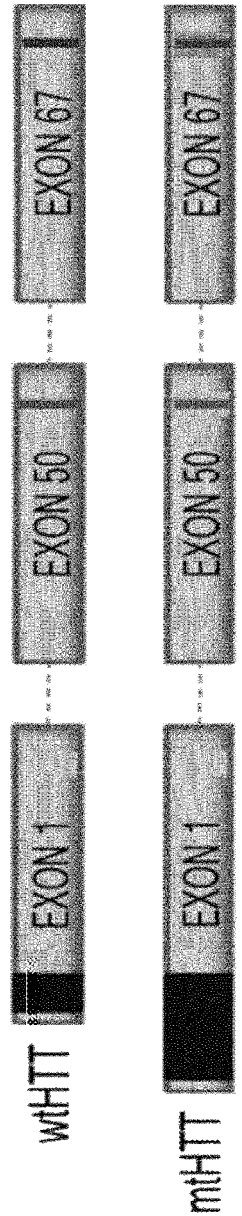
FIGS. 1A-1C. Human huntingtin (HTT) gene and target sequences. (A) Schematic of the human HTT gene (L27350.1) with CAG expansions (black) and target sequences for miH1-H21 (light grey) (B) Exon 1 RNA sequence of the HTT gene (SEQ ID NO. 2). The CAG repeat sequence is from nts. 367-429. (C) Schematic of target sequences tested for exon 1 (H1, 185-205; H2, 186-206; H3, 189-209; H4, 191-211; H5, 194-214; H6, 196-216; H7, 250-270; H8, 261-281, H9, 310-330; H10, 311-331, H11, 339-359, H12, 345-365, H13, 454-474; H14, 459-479; H15, 477-497; H16, 486-506; H17, 492-512; H18, 498-518; H19, 549-569; H20, 557-577; H21, 558-578, H1-H21 corresponding to SEQ ID NOs. 23-43). The sequences depicted are DNA sequences. The numbers refer to the corresponding RNA nucleotide sequences in SEQ ID NO. 2. The corresponding RNA target sequences of SEQ ID NO. 2 have the sequence as listed in C) except that wherein the DNA encodes a "t" the RNA encodes a "U".

SEQ ID NO. 1 (5'-CUUCGAGUCCCUCAAGUCCUU-3') corresponds to a target sequence of the huntingtin gene of exon 1 (SEQ ID NO. 2). Exon 1, as depicted in FIG. 1B has 21 repeat CAG sequences from nt. 367-429. The exon 1 sequence as depicted in FIG. 1B corresponds to a normal huntingtin gene that is not associated with disease. Corresponding mutant huntingtin genes associated with Huntington's disease comprise much more than 21 CAG repeat sequences. As said, with 36 to 39 CAG repeats one may develop signs and symptoms of Huntington's disease, while with 40 or more repeats one almost always develop the disorder. The target sequence SEQ ID NO. 1 is comprised in substantially all exon 1 sequences, irrespective of the number of CAG repeats.

SEQ ID NO. 1 corresponds to nucleotide nrs. 345-365 of SEQ ID NO. 2. 18 different target sequences in exon 1 were tested for targeting using double stranded RNAs that were designed to induce a sequence specific inhibition of SEQ ID NO. 2. (see FIG. 1 and FIG. 3A) and it was found that in particular targeting this sequence from exon 1 was useful in reducing huntingtin gene expression. siRNAs varying in length, i.e. consisting of 19, 20, 21, 22, and 23 consecutive basepairs with 2 nucleotide overhangs in addition were found to be effective against this sequence, as well as two separate miRNA scaffolds carrying a 21 nucleotide sequence complementary to SEQ ID NO. 1 at the guide sequence position (see FIGS. 3A, 3B and 4). Hence, the first RNA sequence that is substantially complementary to the huntingtin target sequence SEQ ID NO. 1 has a sequence length of at least 19 nucleotides.

The first RNA sequence according to the invention is comprised in the guide strand of the double stranded RNA, also referred to as antisense strand as it is complementary ("anti") to the sense target sequence. The second RNA sequence is comprised in the passenger strand, also referred to as "sense strand" as it may have substantial sequence identity with or be identical with the target sequence. The first and second RNA sequences are comprised in a double stranded RNA and are substantially complementary. The said double stranded RNA according to the invention is to induce RNA interference to thereby reduce both huntingtin mutant and wild type gene expression. Hence, it is understood that substantially complementary means that it is not required to have all the nucleotides of the first and second RNA sequences base paired, i.e. to be fully complementary, or all the nucleotides of the first RNA sequence and SEQ ID NO. 1 base paired. As long as the double stranded RNA is capable of inducing RNA interference to thereby sequence specifically target a sequence comprising SEQ ID NO. 1, such substantial complementarity is contemplated in the invention.

Hence, in one embodiment the double stranded RNA according to the invention comprising a first RNA sequence and a second RNA sequence wherein the first and second RNA sequence are substantially complementary, and wherein the first RNA sequence has a sequence length of at least 19 nucleotides and is substantially complementary to SEQ ID NO. 1, is capable of inducing RNA interference to sequence specifically reduce expression of an RNA transcript comprising SEQ ID NO. 1. In a further embodiment, said induction of RNA interference to reduce expression of an RNA transcript comprising SEQ ID NO. 1 means that it is to reduce human Huntingtin gene expression.

One can easily determine whether this is the case by using standard luciferase reporter assays and appropriate controls such as described in the examples and as known in the art (Zhuang et al. 2006 Methods Mol Biol. 2006; 342:181-7). For example, a luciferase reporter comprising SEQ ID No. 1 can be used to show that the double stranded RNA according to the invention is capable of sequence specific knock down. Furthermore, as shown in the example section, Huntingtin expression can be determined with specific antibodies to determine the amount of expression in a western blot analysis, as can northern blot analysis detecting the amount of RNA transcript.

Hence, the double stranded RNA according to the invention is for use in inducing RNA interference. The double stranded RNA according to the invention is for use in reducing expression of transcripts comprising SEQ ID NO. 1, such as for example SEQ ID NO. 2 or the like with varying number of CAG repeats.

As said, the double stranded RNA is capable of inducing RNA interference. Double stranded RNA structures are well known in the art that are suitable for inducing RNAi. For example, a small interfering RNA (siRNA) comprises two separate RNA strands, one strand comprising the first RNA sequence and the other strand comprising the second RNA sequence. An siRNA design that is often used involves 19 consecutive base pairs with 3' two-nucleotide overhangs (see FIG. 2A). This design is based on observed Dicer processing of larger double stranded RNAs that results in siRNAs having these features. The 3'-overhang may be comprised in the first RNA sequence. The 3'-overhang may be in addition to the first RNA sequence. The length of the two strands of which an siRNA is composed may be 19, 20, 21, 22, 23, 24, 25, 26 or 27 nucleotides or more. Each of the two strands comprises the first and second RNA sequence. The strand comprising the first RNA sequence may also consist thereof. The strand comprising the first RNA sequence may also consist of the first RNA sequence and the overhang sequence.

siRNAs may also serve as Dicer substrates. For example, a Dicer substrate may be a 27-mer consisting of two strands of RNA that have 27 consecutive base pairs. The first RNA sequence is positioned at the 3'-end of the 27-mer duplex. At the 3'-end, like the with siRNAs, is a two nucleotide overhang. The 3'-overhang may be comprised in the first RNA sequence. The 3'-overhang may be in addition to the first RNA sequence. 5' from the first RNA sequence, additional sequences may be included that are either complementary to the target sequence adjacent to SEQ ID NO. 1 or not. The other end of the siRNA dicer substrate is blunt ended. This dicer substrate design results in a preference in processing by Dicer such that an siRNA is formed like the siRNA design as described above, having 19 consecutive base pairs and 2 nucleotide overhangs at both 3'-ends. In any case, siRNAs, or the like, are composed of two separate RNA strands (Fire et al. 1998, Nature. 1998 Feb. 19; 391(6669):806-11) each RNA strand comprising or consisting of the first and second RNA sequence according to the invention.

The double stranded RNA according to the invention does not require both first and second RNA sequences to be comprised in two separate strands. The first and second RNA sequences can also be comprised in a single strand of RNA, such as e.g. an shRNA. A shRNA may comprise from 5'-second RNA sequence-loop sequence-first RNA sequence-optional 2 nt overhang sequence-3'. Alternatively, a shRNA may comprise from 5'-first RNA sequence-loop sequence-second RNA sequence-optional 2 nt overhang sequence-3'. Such an RNA molecule forms intramolecular base pairs via the substantially complementary first and second RNA sequence. Suitable loop sequences are well known in the art (i.a. as shown in Dallas et al. 2012 Nucleic Acids Res. 2012 October; 40(18):9255-71 and Schopman et al., Antiviral Res. 2010 May; 86(2):204-11).

The loop sequence may also be a stem-loop sequence, whereby the double stranded region of the shRNA is extended. Without being bound by theory, like the siRNA dicer substrate as described above, a shRNA is usually processed by Dicer to obtain e.g. an siRNA having an siRNA design such as described above, having e.g. 19 consecutive base pairs and 2 nucleotide overhangs at both 3'-ends. In case the double stranded RNA is to be processed by Dicer, it is preferred to have the first and second RNA sequence at the end of A double stranded RNA according to the invention may also be incorporated in a pre-miRNA or pri-mi-RNA scaffold. Micro RNAs, i.e. miRNA, are guide strands that originate from double stranded RNA molecules that are expressed e.g. in mammalian cells. A miRNA is processed from a pre-miRNA precursor molecule, similar to the processing of a shRNA or an extended siRNA as described above, by the RNAi machinery and incorporated in an activated RNA-induced silencing complex (RISC) (Tijsterman M, Plasterk R H. Dicers at RISC; the mechanism of RNAi. Cell. 2004 Apr. 2; 117(1):1-3). Without being bound by theory, a pre-miRNA is a hairpin molecule that can be part of a larger RNA molecule (pri-miRNA), e.g. comprised in an intron, which is first processed by Drosha to form a pre-miRNA hairpin molecule. The pre-miRNA molecule is a shRNA-like molecule that can subsequently be processed by dicer to result in an siRNA-like double stranded duplex. The miRNA, i.e. the guide strand, that is part of the double stranded RNA duplex is subsequently incorporated in RISC. An RNA molecule such as present in nature, i.e. a pri-miRNA, a pre-miRNA or a miRNA duplex, may be used as a scaffold for producing an artificial miRNA that specifically targets a gene of choice. Based on the predicted RNA structure, e.g. as predicted using e.g. m-fold software, the natural miRNA sequence as it is present in the RNA structure (i.e. duplex, pre-miRNA or pri-miRNA), and the sequence present in the structure that is complementary therewith are removed and replaced with a first RNA sequence and a second RNA sequence according to the invention. The first RNA sequence and the second RNA sequence may be selected such that the RNA structures that are formed, i.e. pre-miRNA, pri-miRNA and/or miRNA duplex, resemble the corresponding predicted original sequences. pre-miRNA, pri-miRNA and miRNA duplexes (that consist of two separate RNA strands that are hybridized via complementary base pairing), as found in nature often are not fully base paired, i.e. not all nucleotides that correspond with the first and second strand as defined above are base paired, and the first and second strand are often not of the same length. How to use miRNA precursor molecules as scaffolds for any selected target sequence and substantially complementary first RNA sequence is described e.g. in Liu Y P Nucleic Acids Res. 2008 May; 36(9):2811-24.

In any case, as is clear from the above, the double stranded RNA comprising the first and second RNA sequence can comprise additional nucleotides and/or nucleotide sequences. The double stranded RNA may be comprised in a single RNA sequence or comprised in two separate RNA strands. Without being bound by theory, whatever design is used for the double stranded RNA, it is designed such that an antisense sequence comprising the first RNA sequence of the invention can be processed by the RNAi machinery such that it can be incorporated in the RISC complex to have its action. The said sequence comprising or consisting of the first RNA sequence of the invention being capable of sequence specifically targeting SEQ ID NO. 1. Hence, as long as the double stranded RNA is capable of inducing RNAi, such a double stranded RNA is contemplated in the invention. Hence, in one embodiment, the double stranded RNA according to the invention is comprised in a pre-miRNA scaffold, a pri-miRNA scaffold, a shRNA, or an siRNA.

The term complementary is defined herein as nucleotides of a nucleic acid sequence that can bind to another nucleic acid sequence through hydrogen bonds, i.e. nucleotides that are capable of base pairing. Ribonucleotides, the building blocks of RNA are composed of monomers (nucleotides) containing a sugar, phosphate and a base that is either a purine (guanine, adenine) or pyrimidine (uracil, cytosine). Complementary RNA strands form double stranded RNA. A double stranded RNA may be formed from two separate complementary RNA strands or the two complementary RNA strands may be comprised in one RNA strand. In complementary RNA strands, the nucleotides cytosine and guanine (C and G) can form a base pair, guanine and uracil (G and U), and uracil and adenine (U and A). The term substantial complementarity means that is not required to have the first and second RNA sequence to be fully complementary, or to have the first RNA sequence and SEQ ID NO. 1 to be fully complementary. For example, the first and second nucleotides as shown in FIG. 2A are substantially complementary and not fully complementary.

In one embodiment, the substantial complementarity between the first RNA sequence and SEQ ID NO. 1 consists of having no mismatches, one mismatched nucleotide, or two mismatched nucleotides. It is understood that one mismatched nucleotide means that over the entire length of the first RNA sequence that base pairs with SEQ ID NO. 1 one nucleotide does not base pair with SEQ ID NO. 1. Having no mismatches means that all nucleotides base pair with SEQ ID NO. 1, and having 2 mismatches means two nucleotides do not base pair with SEQ ID NO. 1. The first RNA sequence may also be longer than 21 nucleotides, in this scenario, the substantial complementarity is determined over the entire length of SEQ ID NO. 1. This means that SEQ ID NO. 1 in this embodiment has either no, one or two mismatches over its entire length when base paired with the first RNA sequence. For example, as shown in FIG. 3B and the examples, siRNAs having a first nucleotide sequence length of 22 and 23 nucleotides were tested. These first nucleotide sequences had no mismatches and were fully complementary to SEQ ID NO. 1. Having a few mismatches between the first nucleotide sequence and SEQ ID NO. 1 may be allowed according to the invention, as long as the double stranded RNA according to the invention is capable of reducing expression of transcripts comprising SEQ ID NO. 1, such as a luciferase reporter or e.g. a transcript comprising SEQ ID NO. 1. In this embodiment, substantial complementarity between the first RNA sequence and SEQ ID NO. 1 consists of having no, one or two mismatches over the entire length of either the first RNA sequence or SEQ ID NO. 1, whichever is the shortest.

In one embodiment the first RNA sequence and SEQ ID NO. 1 have at least 15, 16, 17, 18, or 19 nucleotides that base pair. Preferably the first RNA sequence and SEQ ID NO. 1 are substantially complementary, said complementarity comprising at least 19 base pairs. In another embodiment, the first RNA sequence has at least 8, 9, 10, 11, 12, 13 or 14 consecutive nucleotides that base pair with consecutive nucleotides of SEQ ID NO. 1. In another embodiment, the first RNA sequence has at least 19 consecutive nucleotides that base pair with consecutive nucleotides of SEQ ID NO. 1. In another embodiment the first RNA sequence comprises at least 19 consecutive nucleotides that base pair with 19 consecutive nucleotides of SEQ ID NO. 1. In still another embodiment, the first RNA sequence has at least 17 nucleotides that base pair with SEQ ID NO. 1 and has at least 15 consecutive nucleotides that base pair with consecutive nucleotides of SEQ ID NO. 1. The sequence length of the first nucleotide is at most 21, 22, 23, 24, 25, 26, or 27 nucleotides.

As said, a mismatch according to the invention means that a nucleotide of the first RNA sequence does not base pair with SEQ ID NO. 1. Nucleotides that do not base pair are A and C, C and U, or A and G. A mismatch may also result from a deletion of a nucleotide, or an insertion of a nucleotide. When the mismatch is a deletion in the first RNA sequence, this means that a nucleotide of SEQ ID NO. 1 is not base paired with the first RNA sequence when compared with the entire length of the first RNA sequence. Nucleotides that can base pair are A-U, G-C and G-U. A G-U base pair is also referred to as a G-U wobble, or wobble base pair. In one embodiment the number of G-U base pairs between the first RNA sequence and SEQ ID NO. 1 is 0, 1 or 2. In one embodiment, there are no mismatches between the first RNA sequence and SEQ ID NO. 1 and a G-U base pair or G-U pairs are allowed. Preferably, there may be no G-U base pairs between the first RNA sequence and SEQ ID NO. 1, or the first RNA sequence and SEQ ID NO. 1 only have base pairs that are A-U or G-C. Preferably, there are no G-U base pairs and no mismatches between the first RNA sequence and SEQ ID NO. 1. Hence, the first RNA sequence of the double stranded RNA according to invention preferably is fully complementary to SEQ ID NO. 1, said complementarity consisting of G-C and A-U base pairs.

It may be not required to have full complementarity (i.e. full base pairing (no mismatches) and no G-U base pairs) between the first nucleotide sequence and SEQ ID NO. 1 as such a first nucleotide sequence can still allow for sufficient suppression of gene expression. Also, having not full complementarity may be contemplated for example to avoid or reduce off-target sequence specific gene suppression while maintaining sequence specific inhibition of transcripts comprising SEQ ID NO. 1. However, it may be preferred to have full complementarity as it may result in more potent inhibition. Without being bound by theory, having full complementarity between the first RNA sequence and SEQ ID NO. 1 may allow for the activated RISC complex comprising the said first RNA sequence to cleave its target sequence, whereas having mismatches may only allow inhibition of translation, the latter resulting in less potent inhibition.

In one embodiment, the first RNA sequence has a sequence length of at least 19 nucleotides, preferably 20 nucleotides, more preferably of at least 21 nucleotides. The sequence length can also be at least 22 nucleotides, or at least 23 nucleotides. The first RNA sequence according to the invention may be selected from SEQ ID NOs. 3-7.

TABLE 1

First RNA sequences.

| SEQ ID NO. | First RNA sequence | length |
|---|---|---|
| 3 | 5'-AAGGACUUGAGGGACUCGA-3' | 19 |
| 4 | 5'-AAGGACUUGAGGGACUCGAA-3' | 20 |
| 5 | 5'-AAGGACUUGAGGGACUCGAAG-3' | 21 |
| 6 | 5'-AAGGACUUGAGGGACUCGAAGG-3' | 22 |
| 7 | 5'-AAGGACUUGAGGGACUCGAAGGC-3' | 23 |

The first RNA sequences of table 1 have been shown to specifically inhibit transcripts comprising SEQ ID NO. 1 as described in the example section.

In one embodiment, the first nucleotide sequence of the double stranded RNA according to the invention are fully complementary with SEQ ID NO. 1. This means that there are no mismatches between the first RNA sequence and SEQ ID NO. 1 over the entire length of either the first RNA sequence or SEQ ID NO. 1, whichever is the shortest. Preferably, the first nucleotide sequence and SEQ ID NO. 1 are fully complementary, comprising only G-C and A-U base pairs. Preferably, the first RNA sequence is selected from the group consisting of SEQ ID NOs 3-7, which are fully complementary with SEQ ID NO. 1. Most preferably the first RNA sequence is SEQ ID NO. 5. When the first nucleotide sequence is 21 nucleotides or less (SEQ ID NOs. 3, 4 and 5) all nucleotides of the first nucleotide sequence base pair with SEQ ID NO. 1. When the first nucleotide sequence is longer than 21 nucleotides (SEQ ID NOs. 6 and 7), all nucleotides of SEQ ID NO. 1 base pair with the first nucleotide sequence. The additional nucleotides that are comprised in the first RNA sequence do not base pair with SEQ ID NO. 1. When the first nucleotide sequence is longer than 21 nucleotides and the additional nucleotides are to be part of the guide strand, preferably the additional nucleotides are complementary to the sequence flanking sequence of SEQ ID NO. 1 as present in SEQ ID NO. 2.

With regard to the second RNA sequence, the second RNA sequence is substantially complementary with the first RNA sequence. The second RNA sequence combined with the first RNA sequence forms a double stranded RNA. As said, this is to form a suitable substrate for the RNA interference machinery such that a guide sequence derived from the first RNA sequence is comprised in the RISC complex in order to sequence specifically inhibit expression of its target, i.e. Huntingtin gene expression. As said, such double stranded RNA is preferably comprised in a pre-miRNA scaffold, a pri-miRNA scaffold, a shRNA, or an siRNA.

The sequence of the second RNA sequence has similarities with the target sequence. However, the substantial complementarity with the first RNA sequence may be selected to have less substantial complementarity as compared with the substantial complementarity between the first RNA sequence and SEQ ID NO. 1. Hence, the second RNA sequence may comprise 0, 1, 2, 3, 4, or more mismatches, 0, 1, 2, 3, or more G-U wobble base pairs, and may comprise insertions of 0, 1, 2, 3, 4, nucleotides and/or deletions of 0, 1, 2, 3, 4, nucleotides. Preferably the first RNA sequence and the second RNA sequence are substantially complementary, said complementarity comprising 0, 1, 2 or 3 G-U base pairs and/or wherein said complementarity comprises at least 17 base pairs.

These mismatches, G-U wobble base pairs, insertions and deletions, are with regard to the first RNA sequence, i.e. the double stranded region that is formed between the first and second RNA sequence. As long as the first and second RNA sequence can substantially base pair, and are capable of inducing sequence specific inhibition of SEQ ID NO. 1, such substantial complementarity is allowed according to the invention. It is also understood that substantially complementarity between the first RNA sequence and the second RNA sequence may depend on the double stranded RNA design of choice. It may depend for example on the miRNA scaffold that is chosen for in which the double stranded RNA is to be incorporated.

TABLE 2

Second RNA sequences.

| SEQ ID NO. | Second RNA sequence | length |
|---|---|---|
| 8 | 5'-UCGAGUCCCUCAAGUCCUU-3' | 19 |
| 9 | 5'-UUCGAGUCCCUCAAGUCCUU-3' | 20 |
| 10 | 5'-CUUCGAGUCCCUCAAGUCCUU-3' | 21 |
| 11 | 5'-CCUUCGAGUCCCUCAAGUCCUU-3' | 22 |
| 12 | 5'-GCCUUCGAGUCCCUCAAGUCCUU-3' | 23 |
| 13 | 5'-CUUCGAGUCUCAAGUCCUU-3' | 19 |
| 14 | 5'-ACGAGUCCCUCAAGUCCUC-3' | 19 |

In one embodiment, a second RNA sequence is selected from the group consisting of SEQ ID NOs. 8-14. In Table 2, examples of said second RNA sequences in accordance with the invention are listed. SEQ ID NOs. 8, 9, 10, 11 and 12 are fully complementary with SEQ ID NO. 1 over their entire length. SEQ ID NOs. 13 and 14 can be combined with a first nucleotide having a sequence corresponding to SEQ ID NO. 5 of 21 nucleotides, which is complementary with SEQ ID NO. 1 over its entire length. SEQ ID NO. 13 is complementary with SEQ ID NO. 5 having a two nucleotide deletion (resulting in the corresponding 2 nucleotides of SEQ ID NO. 5 not base paired) and 19 nucleotides base paired. SEQ ID NO. 14 is complementary with SEQ ID NO. 5 having a two nucleotides deletion, two mismatches, and 17 nucleotides base paired. The complementarity can also be seen in FIG. 2B, as the combination of SEQ ID NO. 5 and SEQ ID NO. 13 is present in miH12_155, and the combination of SEQ ID NO. 5 and SEQ ID NO. 14 is present in miH12_451a. Hence, as is clear from the above, the second RNA sequence does not require complementarity with the first RNA sequence, but may comprise deletions, insertions and mutations that result in mismatches, as compared with SEQ ID NO. 1.

As is clear from the above, the substantial complementarity between the first RNA sequence and the second RNA sequence, may comprise mismatches, deletions and/or insertions relative to a first and second RNA sequence being fully complementary (i.e. fully base paired). In one embodiment, the first and second RNA sequences have at least 11 consecutive base pairs. Hence, at least 11 consecutive nucleotides of the first RNA sequence and at least 11 consecutive nucleotides of the second RNA sequence are fully complementary. In another embodiment the first and second RNA sequence have at least 15 nucleotides that base pair. Said base pairing between at least 15 nucleotides of the first RNA sequence and at least 15 nucleotides of the second RNA sequence may consist of G-U, G-C and A-U base pairs, or may consist of G-C and A-U base pairs. In still another embodiment, the first and second RNA sequence have at least 15 nucleotides that base pair and have at least 11 consecutive base pairs. In still another embodiment, the first RNA sequence and the second RNA sequence are substantially complementary, wherein said complementarity comprises at least 17 base pairs. Said 17 base pairs may preferably be 17 consecutive base pairs, said base pairing consisting of G-U, G-C and A-U base pairs or consisting of G-C and A-U base pairs.

In one embodiment, the first and second nucleotide sequence are selected from the group of SEQ ID NOs. 3 and 8; 4 and 9; 5 and 10; 5 and 13; 5 and 14; 6 and 11; and 7 and 12. These combinations of first and second nucleotide sequences were shown to be effective when comprised in siRNAs or miRNA scaffolds.

The first and second nucleotide sequences that are substantially complementary preferably do not form a double stranded RNA of 30 consecutive base pairs or longer, as these can trigger an innate immune response via the double-stranded RNA (dsRNA)-activated protein kinase pathway. Hence, the double stranded RNA is preferably less than 30 consecutive base pairs. Preferably, a pre-miRNA scaffold, a pri-miRNA scaffold, a shRNA, or an siRNA comprising the double stranded RNA according to the invention does not comprise 30 consecutive base pairs.

Preferably the double stranded RNA according to the invention is comprised in a pre-miRNA or pri-miRNA scaffold. A pri-miRNA scaffold comprises a pre-miRNA scaffold. The pre-miRNA scaffold comprises the double stranded RNA of the invention, i.e. the first RNA sequence and the second RNA sequence. Preferably, the double stranded DNA according to the invention is comprised in a pri-miRNA scaffold derived from miR-451a (also referred to as miR-451) or miR-155. Examples of double stranded RNAs according to the invention comprised in a pre-miRNA scaffold are depicted in FIG. 2A. The sequence of these pre-miRNAs are listed in table 3 below.

TABLE 3

Pre-miRNA scaffolds with SEQ ID NO. 5

| SEQ ID NO. | Name | Sequence |
|---|---|---|
| 15 | pre-miR451a | 5'-CUUGGGAAUGGCAAGGAAGGACUUGAGGGACUCG AAGACGAGUCCCUCAAGUCCUCUCUUGCUAUACCCAGA-3' |
| 16 | pre-miR155 | 5'-UGCUGAAGGACUUGAGGGACUCGAAGGUUUUGGCCA CUGACUGACCUUCGAGUCUCAAGUCCUUCAGGA-3' |

Figure 2B:
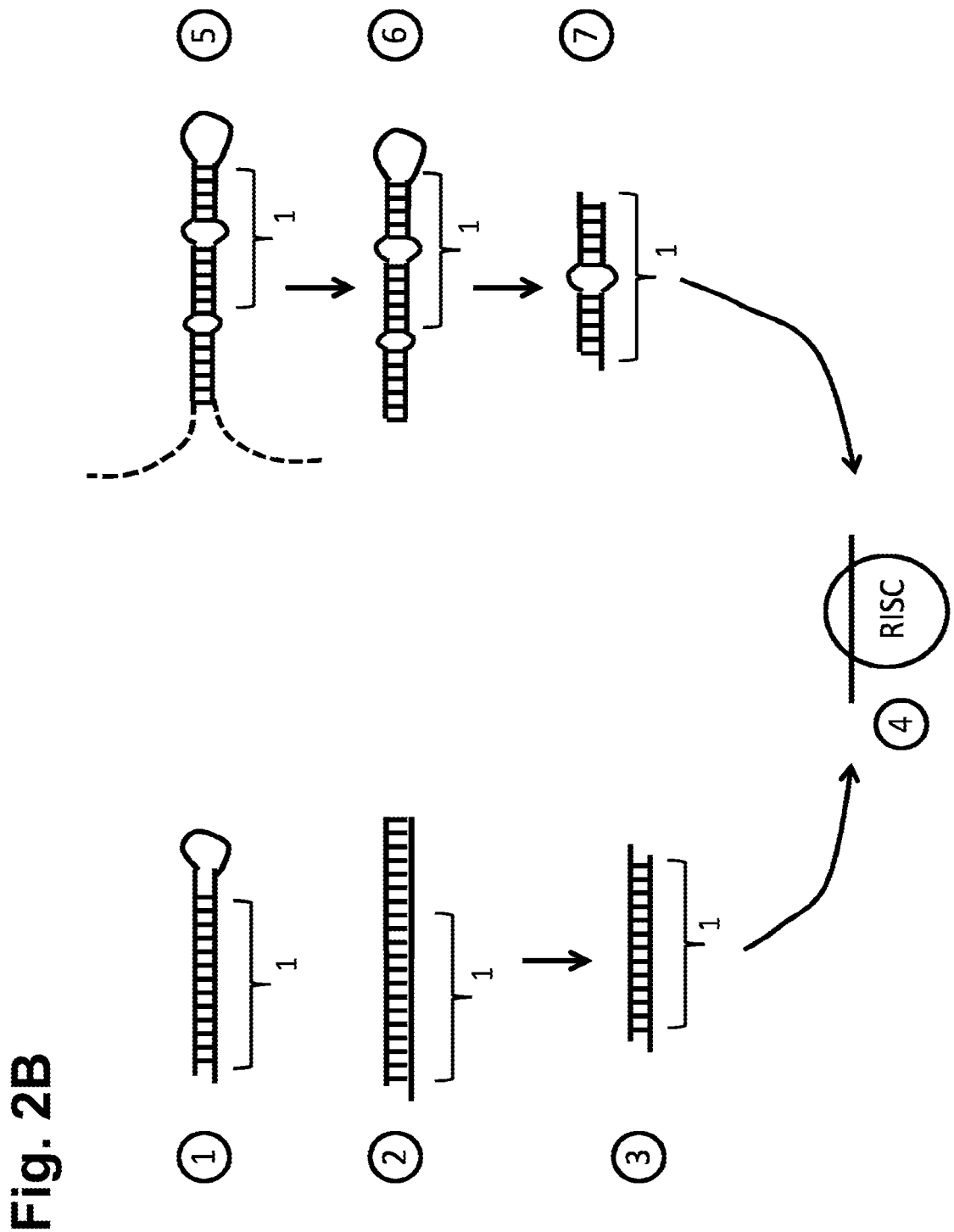

The pre-mRNA sequence of SEQ ID NO. 15 consists of a 5' arm corresponding to nucleotides 1-16 of SEQ ID NO. 15, a first RNA sequence corresponding to SEQ ID NO. 5 from nucleotides 17-37 of SEQ ID NO. 15, a second RNA sequence corresponding to SEQ ID NO. 14 from nucleotides 38-56 of SEQ ID NO. 15, and a 3'-arm corresponding to nucleotides 57-72 of SEQ ID NO. 15. The pre-miR451a scaffold according to the invention comprises the 5'-arm corresponding to nucleotides 1-16 of SEQ ID NO. 15, followed by the first nucleotide sequence according to the invention, the second nucleotide sequence according to the invention, and the 3'-arm corresponding to nucleotides 57-72 of SEQ ID NO. 15. Preferably, the first and second RNA sequences are selected such that when comprised in the pri-miR451a scaffold a predicted structure highly similar or as shown in FIG. 2B is obtained. Preferably the base pairs that are formed between the first and second RNA sequence are G-C, G-U and A-U base pairs and preferably the sequence length of the first RNA sequence is 21 nucleotides and the length of the second RNA sequence is preferably 19 nucleotides. Preferably the base pairs that are formed between the first and second RNA sequence are G-C and A-U base pairs and preferably the sequence length of the first RNA sequence is 21 nucleotides and the length of the second RNA sequence is preferably 19 nucleotides. Without being bound by theory, this pri-R451a scaffold may be preferred as it does not result in a passenger strand to be processed by the RNAi machinery to be incorporated into RISC (Cheloufi et al., 2010 Jun. 3; 465(7298):584-9). From an siRNA or miRNA duplex, in principle both strands can be incorporated into RISC. As the passenger strand (corresponding to the second sequence) may result in targeting of transcripts other than a huntingtin transcript, using the pri-miR451a or pre-miR451a scaffold may allow one to avoid such unwanted targeting. When tested for potential "passenger strand" activity, no activity was detected with a pri-451a scaffold (see FIGS. 4A and 4B). The processing of the pre-miRNA hairpin is understood to be Dicer independent and to be cleaved by Ago2 (Yang et al., Proc Natl Acad Sci USA. 2010 Aug. 24; 107(34):15163-8).

The pre-mRNA sequence of SEQ ID NO. 16 consists of a 5' arm corresponding to nucleotides 1-5 of SEQ ID NO. 16, a first RNA sequence corresponding to SEQ ID NO. 5 from nucleotides 6-26 of SEQ ID NO. 16, a loop sequence from nucleotides 27-45 of SEQ ID NO. 16, a second RNA sequence corresponding to SEQ ID NO. 13 from nucleotides 46-64 of SEQ ID NO. 16, and a 3'-arm corresponding to nucleotides 65-69 of SEQ ID NO. 16. The pre-155 scaffold comprising the first and second RNA sequence according to the invention comprises the 5'-arm corresponding to nucleotides 1-5 of SEQ ID NO. 16, the first RNA sequence, a loop sequence corresponding to nucleotides 27-45 of SEQ ID NO. 16, the second RNA sequence, and a 3'-arm corresponding to nucleotides 65-69 of SEQ ID NO. 16. Preferably, the first and second RNA sequence are selected such that when comprised in the pre-miR155 scaffold (or pri-miRNA scaffold) a predicted structure highly similar as shown in FIG. 2B is obtained. Preferably the base pairs that are formed between the first and second RNA sequence are G-C or A-U base pairs and preferably the sequence length of the first RNA sequence is 21 nucleotides and the length of the second RNA sequence is preferably 19 nucleotides. Said 19 nucleotides are preferably fully complementary with nucleotides 2-18 of a first nucleotide sequence of 21 nucleotides in length.

A pre-miRNA sequence when comprised in a larger RNA sequence requires 5'- and 3'-single stranded flanking sequences that allow Drosha recognition and cleavage. Said sequences that are suitable to allow for Drosha recognition and cleavage are 5'-pri-miRNA sequence and the 3'-pri-miRNA sequence. For example, the expressed pre-miH12_155 sequence as depicted in FIG. 5A is flanked by 5'-pri-miRNA and the 3'-pri-miRNA sequences of miR155 in the expression vector CMV-miH12-155 (FIG. 2C). The pri-miRNA sequence comprising the miRH12_155 is listed in FIG. 2F, the 5'-pri-miRNA corresponding to nucleotides 1-87 and the 3'-pri-miRNA corresponding to 147-272. Likewise, the CAG-miH12-451 and PGK-miH12-451 pri-miRNA sequences that are expressed by their respective vectors in FIGS. 2D and 2E are shown in FIGS. 2G and 2H. The 5'-pri-miRNA and the 3'-pri-miRNA of the expressed CAG-miH12-451 RNA corresponding to nucleotides 1-302 and 375-605, and the 5'-pri-miRNA and the 3'-pri-miRNA of the expressed of PGK-miH12-451 RNA corresponding respectively to nucleotides 1-516 and 589-819. The length of the single-stranded flanks can vary but is typically around 80 nt (Zeng and Cullen, J Biol Chem. 2005 Jul. 29; 280(30): 27595-603; Cullen, Mol Cell. 2004 Dec. 22; 16(6):861-5) The minimal length of the single-stranded flanks can easily be determined as when it becomes too short, Drosha processing may fail and sequence specific inhibition will be reduced or even absent. In one embodiment, the pri-miRNA scaffold carrying the first and second RNA sequence according to the invention has a 5'-sequence flank and a 3' sequence flank relative to the predicted re-miRNA structure of at least 50 nucleotides. The pre-miRNA and the pri-miRNA derived sequences are preferably all derived from the same naturally occurring pri-miRNA sequence.

The pre-miRNA sequence of SEQ ID NO. 15 and SEQ ID NO. 16 are encoded by the DNA sequences as depicted in FIGS. 2C (SEQ ID NO. 16), 2D (SEQ ID NO. 15), and 2E (SEQ ID NO. 15). Pri-miRNA sequences comprising said pre-miRNA sequences are depicted in FIGS. 2F (SEQ ID NO. 16), G (SEQ ID NO. 15) and H (SEQ ID NO. 15). The pri-miRNA encoded by CMV-miH12-155 correspond to nucleotides 1433-1704 of FIG. 2C, of CAG-miH12-451 to nucleotides 1716-2320 of FIG. 2D and of PGK-miH12-451 to nucleotides 278-1097 of FIG. 2E. Likewise, the first and second RNA sequences are to be incorporated as described above for the pre-miRNAs.

The double stranded RNAs according to the invention, incorporated in an siRNA, shRNA, pri-mRNA scaffold or pre-miRNA scaffold can be provided in a cell using methods known in the art, such as lipofection, transfection or using any other suitable means therefor. The double stranded RNAs according to the invention may be synthetic double stranded RNAs or natural double stranded RNAs. Synthetic double stranded RNAs and may comprise nucleic acids containing known analogs of natural nucleotides. The said double stranded RNA has similar properties as compared to their natural counterparts and an RNA interference activity similar to or improved over double stranded RNAs that consist entirely of non-synthetic double stranded RNA. For example, synthetic siRNAs may include in their design the use of Locked Nucleic Acid (a ribose ring connected by a methylene bridge (orange) between the 2'-0 and 4'-C atoms), modified nucleotides such as nucleotides comprising phosphorothioates, 2'-O-Me, 2'-O-allyl and 2'-deoxy-fluorouridine. It is well known that double stranded RNAs, e.g. siRNAs, can accommodate quite a number of modifications at both base-paired and non-base-paired positions without significant loss of activity. Preferably, the double stranded RNA of the invention is a double stranded RNA that consists of natural nucleotides, such as obtained from expression of a double stranded RNA from.

Hence, in one embodiment, the said double stranded RNAs of the invention are encoded by a DNA sequence. The said DNA sequence encoding the said double stranded RNA, e.g. as comprised in an siRNA, shRNA, pri-mRNA scaffold or pre-miRNA scaffold, is comprised in an expression cassette. It is understood that when the double stranded RNA is to be e.g. an siRNA, consisting of two RNA strands, that there are two expression cassettes required. One encoding an RNA strand comprising the first RNA sequence, the other cassette encoding an RNA strand comprising the first RNA strand. When the double stranded RNA is comprised in a single RNA molecule, e.g. encoding a shRNA, pre-miRNA or pri-miRNA, one expression cassette may suffice. A pol II expression cassette may comprise a promoter sequence a sequence encoding the RNA to be expressed followed by a polyadenylation sequence. In case the double stranded RNA that is expressed comprises a pri-miRNA scaffold, the encoded RNA sequence may encode for intron sequences and exon sequences and 3'-UTR's and 3'-UTRs. A pol III expression cassette in general comprises a promoter sequence, followed by the DNA sequence encoding the RNA (e.g. shRNA sequence, pre-miRNA, or a strand of the double stranded RNAs to be comprised in e.g. an siRNA or extended siRNA). A pol I expression cassette may comprise a pol I promoter, followed by the RNA encoding sequence and a 3'-Box. Expression cassettes for double stranded RNAs are well known in the art, and any type of expression cassette can suffice, e.g. one may use a pol III promoter, a pol II promoter or a pol I promoter (i.a. ter Brake et al., Mol Ther. 2008 March; 16(3):557-64, Maczuga et al., BMC Biotechnol. 2012 Jul. 24; 12:42). Examples of expression cassettes expressing a double stranded RNA according to the invention are depicted in FIGS. 2C-E.

Preferably a pol II promoter is used, such as the PGK promoter, a CBA promoter or a CMV promoter (see FIGS. 2C-D). As Huntington's disease affects neurons, it may in particularly be useful to use a neurospecific promoter. Examples of suitable neurospecific promoters are Neuron-Specific Enolase (NSE), human synapsin 1, caMK kinase and tubuline. Other suitable promoters that can be contemplated are inducible promoters, i.e. a promoter that initiates transcription only when the host cell is exposed to some particular stimulus.

Said expression cassettes according to the invention can be transferred to a cell, using e.g. transfection methods. Any suitable means may suffice to transfer an expression cassette according to the invention. Preferably, gene therapy vectors are used that stably transfer the expression cassette to the cells such that stable expression of the double stranded RNAs that induce sequence specific inhibition of the huntingtin gene as described above can be achieved. Suitable vectors may be lentiviral vectors, retrotransposon based vector systems, or AAV vectors. It is understood that as e.g. lentiviral vectors carry an RNA genome, the RNA genome will encode for the said expression cassette such that after transduction of a cell, the said DNA sequence and said expression cassette is formed. Preferably a viral vector is used such as AAV. Preferably the AAV vector that is used is an AAV vector of serotype 5. AAV of serotype 5 may be in particularly useful for transducing neurons as shown in the examples. The production of AAV vectors comprising any expression cassette of interest is well described in; WO2007/046703, WO2007/148971, WO2009/014445, WO2009/104964, WO2011/122950, WO2013/036118, which are incorporated herein in its entirety.

AAV sequences that may be used in the present invention for the production of AAV vectors, e.g. produced in insect or mammalian cell lines, can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). AAV serotypes 1, 2, 3, 4 and 5 are preferred source of AAV nucleotide sequences for use in the context of the present invention. Preferably the AAV ITR sequences for use in the context of the present invention are derived from AAV1, AAV2, and/or AAV5. Likewise, the Rep52, Rep40, Rep78 and/or Rep68 coding sequences are preferably derived from AAV1, AAV2 and AAV5. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

In another embodiment, a host cell is provided comprising the said DNA sequence, or said expression cassette according to the invention. For example, the said expression cassette or DNA sequence may be comprised in a plasmid contained in bacteria. Said expression cassette or DNA sequence may also be comprised in a production cell that produces e.g. a viral vector.

As shown in the example section, and as explained above, the double stranded RNA according to the invention, the DNA sequence according to invention, the expression cassette according to the invention and the gene therapy vector according to the invention are for use in a medical treatment, in particular for use in the treatment of Huntington's disease. Said medical treatment when using an AAV vector (or likewise for a gene therapy vector) comprising a direct infusion of AAV vector of the invention into the brain. Said direct infusion in further embodiments comprising an intrathecal infusion of the vector into the cerebrospinal fluid. Such an intrathecal infusion represents an efficient way to deliver the gene therapy vector to the CNS and to target the neurons. Preferably striatal and cortical structures are targeted via intrastriatal convection enhanced diffusion (CED) delivery of AAV vectors through injections into the striatum. More preferably, for a larger coverage of the CNS, injections are into the striatum and into the thalamus as well. Hence, AAV vectors are delivered intrastriatally, or delivered intrastriatally and intrathalamically through convection enhanced diffusion (CED) injections in the striatum, or the striatum and the thalamamus. Such injections are preferably carried out through MRI-guided injections. Said methods of treatments are in particular useful for human subjects having Huntington's disease. It is understood that the treatment of Huntington's disease involves human subjects having Huntington's disease including human subjects having a genetic predisposition of developing Huntington's disease that do not yet show signs of the disease. Hence, the treatment of human subjects with Huntington's disease includes the treatment of any human subject carrying an Huntingtin allele with more than 35 CAG repeats.

Embodiments

1. A double stranded RNA comprising a first RNA sequence and a second RNA sequence wherein the first and second RNA sequence are substantially complementary, wherein the first RNA sequence has a sequence length of at least 19 nucleotides and is substantially complementarity to SEQ ID NO. 1.
2. A double stranded RNA according to embodiment 1, wherein said double stranded RNA is capable of reducing huntingtin gene expression.
3. A double stranded RNA according to embodiment 1 or embodiment 2, wherein the double stranded RNA is comprised in a pre-miRNA scaffold, a pri-miRNA scaffold, a shRNA, or an siRNA, preferably a pre-miRNA scaffold.
4. A double stranded RNA according to any one of embodiments 1-3, wherein the first RNA sequence has a sequence length of at least 20 nucleotides, preferably of at least 21 nucleotides.
5. A double stranded RNA according to any one of embodiments 1-4, wherein the first RNA sequence is fully complementary to SEQ ID. NO. 1.
6. A double stranded RNA according to any one of embodiments 1-5 wherein the first strand is selected from the group consisting of SEQ ID NO. 3, SEQ ID NO. 4, SEQ ID NO. 5, SEQ ID NO. 6, and SEQ ID NO. 7.
7. A double stranded RNA according to any one of embodiments 1-6, wherein the first strand and second strand are selected from the group consisting of the combinations of SEQ ID NO. 3 and 8; SEQ ID NO. 4 and 9; SEQ ID NO. 5 and 10; SEQ ID NO. 5 and 13; SEQ ID NO. 5 and 14; SEQ ID NO. 6 and 11; and SEQ ID NO. and 7 and 12.
8. A double stranded RNA according to any one of embodiments 1-7, wherein the double stranded RNA is comprised in a pre-miRNA scaffold derived from miR-451a or miR-155.
9. A DNA sequence encoding the double stranded RNA according to any one of embodiments 1-8.
10. An expression cassette encoding a double stranded RNA in accordance with any one of embodiments 1-9.
11. An expression cassette according to embodiment 10, wherein the expression cassette comprises the PGK promoter, a CMV promoter, a neurospecific promoter or a CBA promoter.
12. A gene therapy vector comprising the expression cassette according to embodiment 10 or 11.
13. A gene therapy vector according to embodiment 12, wherein the gene therapy vector is an AAV vector, preferably an AAV vector of serotype 5.
14. A host cell comprising the DNA sequence according to embodiment 9 or the expression cassette according to embodiment 10 or embodiment 11.
15. A double stranded RNA according to any one of embodiments 1-8, a DNA sequence according to embodiment 9, an expression cassette according to embodiment 10 or embodiment 11, a gene therapy vector according to embodiment 12 or embodiment 13, for use in a medical treatment.
16. A double stranded RNA according to any one of embodiments 1-8, a DNA sequence according to embodiment 9, an expression cassette according to embodiment 10 or embodiment 11, a gene therapy vector according to embodiment 12 or embodiment 13, for use in the treatment of Huntington's disease.

Examples miRNA Scaffold Expression Constructs & siRNAs

Figure 1C:
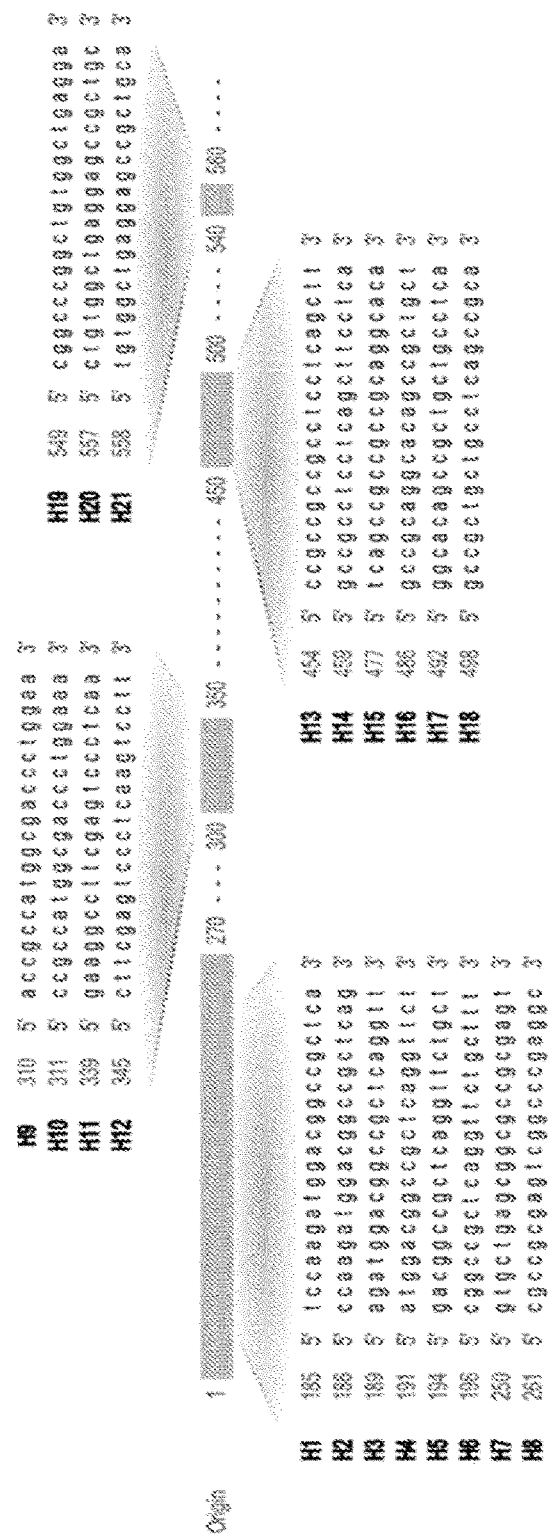

To create miRNA scaffold vectors based on miR155, 21 nucleotide (bp) sequences fully complementary with the selected target sequences in HTT as indicated in FIG. 1, were embedded into the pri-mir-155 backbone of pcDNA6.2-GW/EmGFP-miR (Invitrogen, Carlsbad, Calif.) resulting in pVD-CMV-miHTT-155 (an example of an expression cassette sequence is depicted in FIG. 2C, the pre-miRNA and pri-miRNA sequence as comprised in the expressed RNA are depicted in FIGS. 2B and 2F, respectively). The pri-mir-155 constructs were designed based on the instructions provided by Invitrogen (BLOCK-iT, Pol II miR RNAi expression Vector Kits, Verson E, Jun. 22, 2007, 25-0857) by annealing synthetic double-stranded oligonucleotides in the Bsal site of pcDNA6.2-GW/emGFP-mir155. The structure of all artificial pre-miRNA as encoded by the miHtt constructs was verified using the Mfold software (Nucleic Acids Res. 31 (13), 3406-15, (2003), using mfold version 3.5, as available online on http://mfold.rna.albany.edu/?q=mfold). The predicted structure of the pre-miRNA-155 scaffold carrying the sequence corresponding with SEQ ID NO. 5 is shown in FIG. 2B. The DNA sequence encoding the expression construct for the pri-miRNA-155 scaffold with SEQ ID NO. 5 as a selected first sequence is listed in FIG. 2C (SEQ ID NO. 17), this construct is also referred to as miH12 and its target H12. For the other 20 selected target sequences, the sequences were designed to be fully complementary with the target sequences as depicted in FIG. 1, and the miRNA scaffold having the same structural features as depicted in FIG. 2B, i.e. the second RNA sequence embedded in the scaffold corresponds to the sequence to which the first RNA sequence selected is fully complementary, but having a 2 nucleotide deletion in the center. As a control similarly, a scrambled RNA sequence was used as a first RNA sequence, and like above, a second RNA sequence was designed to create a vector pVD-CMV-miScr-155. The constructs contained GFP for allowing both miRNA expression and transduction visualization in vitro and in vivo.

A miRNA scaffold vector based on miR451a was created. The DNA sequence encoding the pri-miR-451 scaffold was synthesized based on the predicted mature mir-451 sequence being replaced by the H12 targeting sequence, i.e. SEQ ID NO. 5 as first RNA sequence. The second RNA sequence was designed to be fully complementary to nucleotides 2-18 of the first RNA sequence. The second RNA sequence was selected such that the predicted RNA structure of the artificial pre-miRNA sequence adopted a similar structure as the original wild-type structure. The structure of the pre-miRNA as encoded by the constructs was verified using the Mfold software (Nucleic Acids Res. 31 (13), 3406-15, (2003), using mfold version 3.5, as available online on http://mfold.rna.albany.edu/?q=mfold). The predicted structure using SEQ ID NO. 5 is shown in FIG. 2B. Two different miR451a scaffolds expressing vectors were made. The DNA sequences of the expression constructs are depicted in FIGS. 2D and 2E, the corresponding respective pri-miRNA scaffold sequences as comprised in the expressed RNA are listed in FIGS. 2G and 2H. FIG. 2D shows the DNA sequence of the expression cassette of pVD-CAG-miH12-451, which expresses the miRNA scaffold with a CAG promoter, and in FIG. 2E the DNA sequence of the expression cassette of pVD-PGK-miH12-451 is shown, which uses a PGK promoter.

Synthetic siRNA targeting HTT at the miH12 target, i.e. SEQ ID NO. 1, were designed with lengths of 19-23 bp (Table 1). The siRNAs comprised first and second nucleotide sequence corresponding to SEQ ID NOs. 3 and 8; 4 and 9; 5 and 10; 6 and 11; and 7 and 12. The siRNAs were designed to have 3'-UU overhangs in both strands.

Reporter Constructs

The psiCheck-2 constructs LucHTT containing the complete HTT exon 1 sequence was designed and cloned following the instructions as provided by Promega (siCHECK™ Vectors, C8011, Promega Benelux b.v., Leiden, The Netherlands). LucHTT comprises SEQ ID NO. 1 and flanking sequences thereof as present in SEQ ID NO. 2 (see FIG. 1B). The LucH12_451a reporter comprises the sequence complementary to the second RNA sequence as designed to be expressed by pVD-CAG-miH12-451 and pVD-PGK-miH12-451. All constructs have been sequenced, and the correct sequence has been verified. The knockdown efficacy of all miRNA scaffolds and siRNAs were determined on specific luciferase reporters in vitro. Hek293T cells were co-transfected with the miHtt and the Luciferase reporter in a 1:1 ratio (miR-155, PGK-miH12-451), or 1:10 ratio (CAG-miH12-451, i.e. the CAG promoter is very strong). Renilla luciferase knockdown was measured 48 h post transfection (p.t.), and Firefly was measured as an internal control. miScr was used as a negative control and was set at 100%.

In Vitro Results

Among the miH1-miH21 constructs targeting exon 1, miH12 induced the strongest Luciferase reporter knockdown with a 75-80% reduction (FIG. 3A). siRNAs targeting H12, i.e. SEQ ID NO. 1, were all shown to have similar knockdown efficiency, showing upon an increase in dose a stronger knockdown. SiRNAs of 19 and 21 base pairs showed some more inhibition as compared to the other siRNAs tested. Next generation sequencing (NGS) analysis of the RNA expressed from pVD-CMV-miHTT-155 was performed and showed a preference in guide and passenger strands (see e.g. FIG. 2B (7)) corresponding to the first RNA and second RNA sequence as designed to be part of the miRNA scaffold. The pVD-CAG-miH12-451 and pVD-PGK-miH12-451 were tested for targeting both LucHTT and LucH12_451a. Both the CAG and PGK constructs showed sequence specific inhibition (FIG. 4A), whereas a Luc reporter was comprising a sequence fully complementary to the second RNA sequence of the constructs was not reduced.

In Vivo Knockdown Using AAV Vectors in Mice

The expression construct CMV-miH12-155 from pVD-CMV-miHTT-155 was cloned in an AAV5 vector backbone and AAV5 produced using the baculovirus production system. As a control CMV-miScr-155 was also incorporated in an AAV5 backbone to serve as a negative control. For monitoring the brain transduction efficiency, the expression cassettes contained GFP (FIG. 5A). An AAV-5 vector carrying a luciferase reporter construct, Luc73QHTT, comprising the target sequence SEQ ID NO. 1 (i.e. the complete HTT exon 1 sequence with 73 CAG repeats) and flanking sequences thereof as present in SEQ ID NO. 2 (see FIG. 1B). Balb/6 mice (N5) were co-injected intrastriatally with 2 µl of AAV5-Luc73QHtt/SNP ($3.6 \times 10^{12}$ gc/ml), and AAV5-miScr ($1.8 \times 10^{13}$ gc/ml) or AAV5-miH12 ($1.8 \times 10^{13}$ gc/ml) in a 1:5 ratio. A separate group was injected with AAV5-Luc73QHtt/SNP and PBS. Luciferase expression was monitored at 2, 4, and 6 p.i. by MS.). Already at 1 week p.i., there was a clear knockdown of Luc19QHtt/wt by miH12 compared to miScr and Luc19QHtt/wt-only animals (FIGS. 7b and c). A trend was shown indicating a significant decrease in Luciferase reporter expression in time, being almost undetectable (miH12 #1 and #2) in the brain compared with the control groups indicating a strong knockdown of the HTT target by CMV-miH12-155. At the end of the experiment, the Luc73QHtt/SNP fluorescence in the CMV-miH12-155 group was about 1 log lower compared to miScr.

In Vivo Knockdown Using AAV Vectors in an HD Animal Models

Figure 6A:
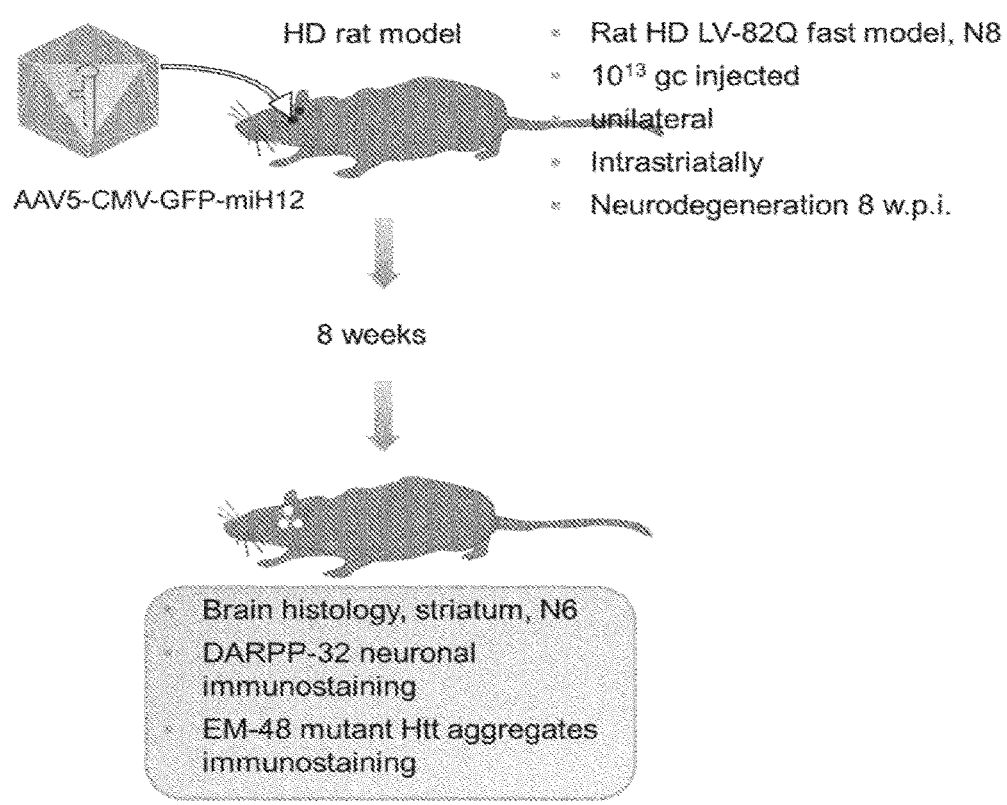
Figure 6B:
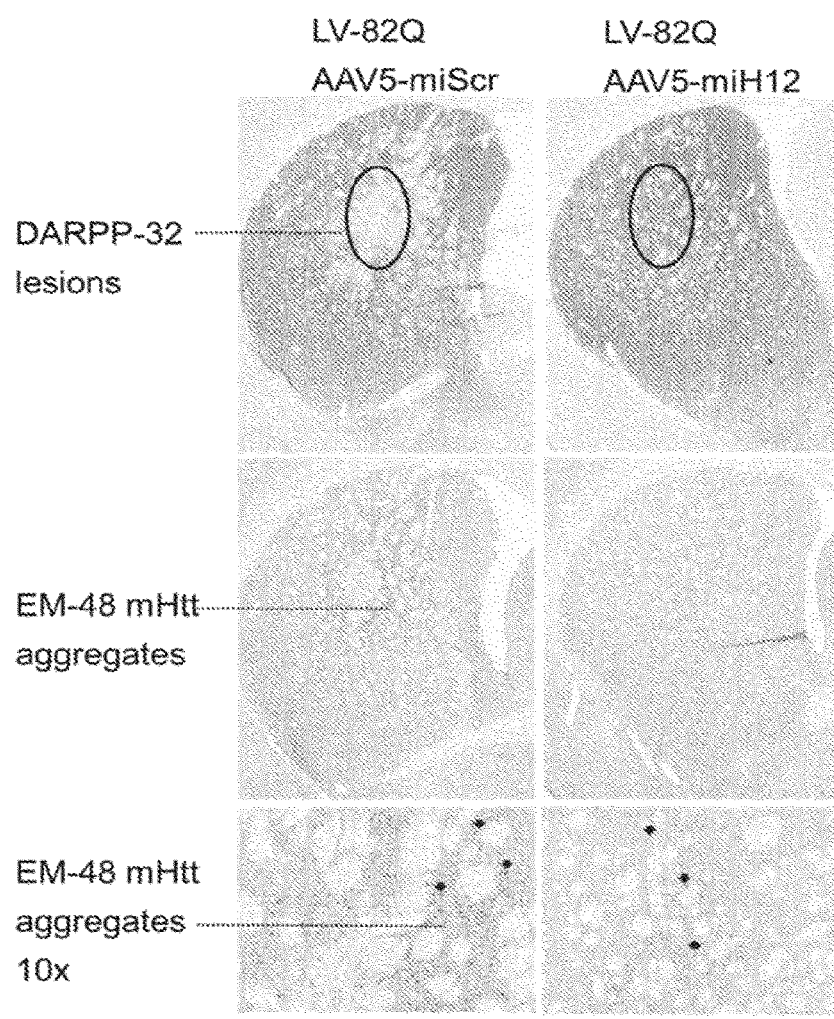
Figure 6C:
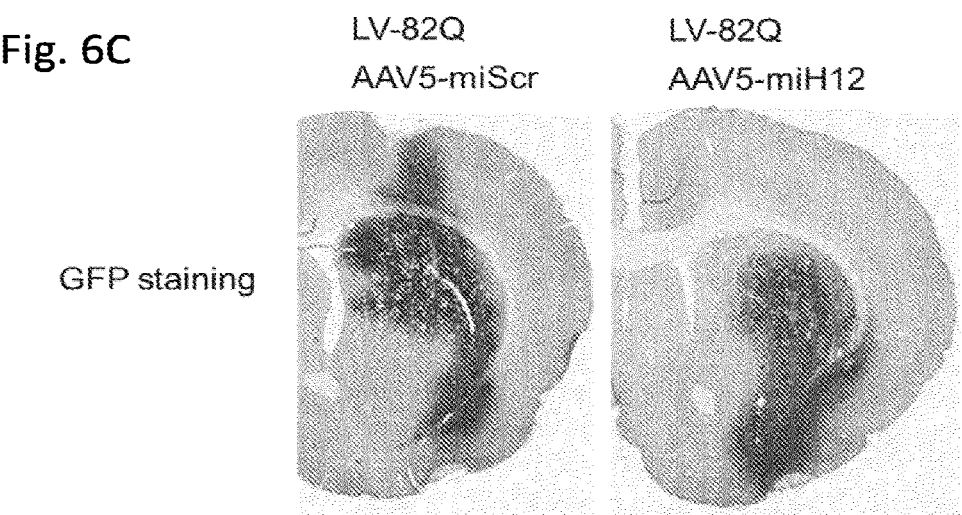
Figure 6D:
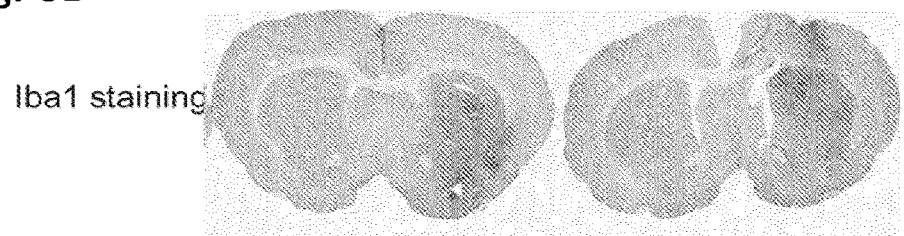

AAV5-CMV-miH12-155 was tested in the LV-171-82Q HD rat model (Drouet et al. 2009, Ann Neurol. 2009 March; 65(3):276-85). The model is based on the striatal overexpression of the first 171 amino acids of the HTT mutant fragment with 82 CAG repeats linked to a fragment of exon 67 containing the SNP C/T. HD rats were injected with AAV5-CMV-miH12-155 or a control AAV5-CMV-miScr-155 (FIG. 6A). Rats were injected intrastriatally with LV-171-82Q and one week later with AAV5-CMV-miH12-155 or AAV5-CMV-miScr-155. The neuro-protective effect of AAV5-CMV-miH12-155 was determined based on histological staining (DARP32, EM48, GFP and Iba1) of HD rat brain sections at the early and late time points (FIGS. 6B, 6C and 6D, 2 weeks p.i.). DARP32 lesions (FIG. 6B, upper panel) indicate neurodegeneration and can be observed as white spots on the brain sections. The panel clearly shows less neuronal death and hence no white spots in the brain sections of AAV5-CMV-miH12-155 rats. Brain sections were stained for mutant HTT aggregates (EM48, FIG. 6B) seen as small brown dots on the slides. There was clearly less neurodegeneration and less mutant HTT aggregates in HD rats injected with AAV5-CMV-miH12-155 as compared to the control group (FIG. 6B, middle and lowest panels). Similar results were obtained at the late time point of 8 weeks post-injection (data not shown). GFP histology (brown staining) results indicated efficient striatal transduction with all vectors used in the current study (FIG. 6C). Additionally, almost no immune response was detected at 8 weeks p.i. based on Iba1 staining (FIG. 6D).

AAV5-CMV-miH12-155 was subsequently further tested in the humanized Hu97/18 HD mouse model (Southwell et al. 2013, Hum Mol Genet. 2013 Jan. 1; 22(1):18-34). This model has the murine Hdh gene replaced by two copies of the human HTT, one carrying 97 CAG repeats and the other 18. Detailed characterization of the motor, psychiatric, cognitive, electrophysiological, neuropathological and biochemical changes in the Hu97/18 mouse model as a result of disease progression has been performed. AAV5-CMV-miH12-155 was injected in 2-months old humanized Hu97/18 HD mouse model by delivery via intracerebral delivery via convection-enhanced diffusion (IC-CED) in the striatum or slow (IC-slow delivery) in the striatum or intracerebroventricular delivery (ICV) in the ventricles of the brain. GFP fluorescence indicated complete transduction of the mouse striatum upon slow and CED delivery (FIG. 7A). Western blot analysis of the human HTT showed knockdown by AAV5-CMV-miH12-155 in the striatum when the CED delivery was applied (FIG. 7B).

Comparison H12 with Prior Art Target Sequences

Target sequences from prior art in the proximity of the H12 sequence were compared with the H12 sequences. siRNAs and miRNA scaffolds were constructed and a direct comparison was carried out using the Luciferase reporter system as described above. Low concentrations of siRNAs were transfected (0.25 nM) in triplicates in order to avoid off-target effects skewing the results. The siRNAs were made with fully complementary guide and passenger strands (G-C and A-U base pairs) and having a UU-3' overhang in both strands. A scrambled siRNA was used as a control and values were measured relative to control. The H12 siRNA showed strongest inhibition (see FIG. 8A). Likewise, miRNA scaffolds were made based on miR-155 as described above in accordance with the instructions of Invitrogen and a direct comparison was made as well. The R6.1 and R6.2 scaffolds were made by replacing 19 and 18 nucleotides that are perfectly complementary to R6.1 and R6.2 target sequences into the guide sequence of the engineered miR-155 scaffold from Invitrogen. Therefore, depending on the pre-miRNA processing by Dicer, the processed R6 guide strand may contain nucleotides from miR-155 scaffold at the end(s) of the sequence. miRNA scaffolds were transfected as described above using different ratios between miRNA construct and reporter (miRNA scaffold construct: Luciferase reporter). A scrambled miRNA construct was used as a control and values were measured relative to control. FIG. 8B shows a 1:1 ratio, whereas FIG. 8C shows a 1:10 ratio. The H12 miRNA scaffold showed strongest inhibition. H12 showed pronounced strong inhibition for both siRNAs and miRNAs, in particular at low concentrations which may be considered most relevant for in vivo application.

TABLE 4

Targets from prior art compared with H12. The target sequences are shown. The target nucleotides that have identity with the H12 target sequence are underlined. (SI. indicates SEQ ID NO.; L. indicates the nucleotide length, Id. Indicates the number of nucleotides that have identity with H12). (R1 is derived from the siRNA siHUNT-2 from Rodriguez-Lebron et al., 2005, Mol Ther. Vol 12 No. 4: 618-633, R2 is derived from an expressed shRNA shD2 from Franich et al., 2008, Mol Ther, Vol. 16 No. 5; 947-956), R3 is derived from the siRNA-DExon1 from US20080015158, R4 is derived from HDAS 07 WO2008134646, R6.1 and R6.2 are derived from a list of about 1750 hypothetical siRNAs designed to target the huntingtin gene (WO2005105995).

| Target | Target sequence | SI. | L. | Id. |
|---|---|---|---|---|
| H12 | 5'-CUUCGAGUCCCUCAAGUCCUU-3' | 34 | 21 | 21 |
| H11 | 5'-GAAGGCCUUCGAGUCCCUCAA-3' | 33 | 21 | 15 |
| R1 (siHUNT-2) | 5'-GGCCUCGAGUCCCUCAAGUCC-3' | 46 | 21 | 18 |
| R2 (shD2) | 5'-GGCCUUCGAGUCCCUCAAGUC-3' | 47 | 21 | 18 |
| R3 (siRNA-DExon1) | 5'-AGGCCUUCGAGUCCCUCAAGU-3' | 48 | 21 | 17 |
| R4 (HDAS 07) | 5'-AUGAAGGCCUUCGAGUCCCUC-3' | 49 | 21 | 13 |
| R6.1 (54) | 5'-GCCUUCGAGUCCCUCAAGU-3' | 50 | 19 | 17 |
| R6.2 (55) | 5'-CCUUCGAGUCCCUCAAGU-3' | 51 | 18 | 17 |

The invention claimed is:

1. A method of reducing expression of an RNA transcript comprising SEQ ID NO:1 in a neuron, method comprising introducing into the neuron a double stranded RNA comprising a first RNA sequence and a second RNA sequence wherein the first and second RNA sequence are substantially complementary, wherein the first RNA sequence comprises SEQ ID NO:3, SEQ ID NO:4, SEQ ID NO:5, SEQ ID NO:6, or SEQ ID NO:7.

2. The method of claim 1, wherein the double stranded RNA is comprised in a pre-miRNA scaffold, a pri-miRNA scaffold, a shRNA, or an siRNA.

3. The method of claim 1, wherein the first RNA sequence comprises 19-27 nucleotides.

4. The method of claim 1, wherein the double stranded RNA is encoded by an expression cassette.

5. The method of claim 4, wherein the expression cassette comprises a neuron-specific promoter.

6. The method of claim 1, wherein the first strand and second strand are respectively selected from the group consisting of SEQ ID NOs: 3 and 8; SEQ ID NOs: 4 and 9; SEQ ID NOs: 5 and 10; SEQ ID NOs: 5 and 13; SEQ ID NOs: 5 and 14; SEQ ID NOs: 6 and 11; and SEQ ID NOs: and 7 and 12.

7. The method of claim 1, wherein the double stranded RNA is comprised in a pre-miRNA scaffold derived from miR-451a or miR-155.

8. The method of claim 1, wherein the double stranded RNA is introduced into the neuron through transduction by a viral vector.

9. The method of claim 8, wherein the viral vector is an adeno associated viral (AAV) vector.

10. The method of claim 9, wherein the AAV vector is a serotype 5 vector.

11. A method of treating a subject with Huntington's disease or a subject that is genetically predisposed for Huntington's disease who does not yet show symptoms of Huntington's disease, comprising administering to a subject with Huntington's disease an effective amount of a viral vector encoding a double stranded RNA comprising a first RNA sequence and a second RNA sequence wherein the first and second RNA sequence are substantially complementary, wherein the first RNA sequence comprises SEQ ID NO:3, SEQ ID NO:4, SEQ ID NO:5, SEQ ID NO:6, or SEQ ID NO:7.

12. The method of claim 11, wherein the viral vector is an adeno associated viral (AAV) vector.

13. The method of claim 11, wherein the AAV vector is a serotype 5 vector.

14. The method of claim 11, wherein the double stranded RNA is comprised in a pre-miRNA scaffold, a pri-miRNA scaffold, a shRNA, or an siRNA.

15. The method of claim 11, wherein the viral vector is administered directly into the central nervous system (CNS).

16. The method of claim 15, wherein administration in the CNS comprises intrathecal infusion or injection into at least one of the striatum and thalamus.

17. The method of claim 11, wherein the double stranded RNA is encoded by an expression cassette in the viral vector.

18. The method of claim 17, wherein the expression cassette comprises a neuron-specific promoter.

* * * * *

SEQUENCE LISTING

<160> NUMBER OF SEQ ID NOS: 51

<210> SEQ ID NO 1
<211> LENGTH: 21
<212> TYPE: RNA
<213> ORGANISM: homo sapiens

<400> SEQUENCE: 1
cuucgagucc cucaaguccu u                                          21

<210> SEQ ID NO 2
<211> LENGTH: 614
<212> TYPE: RNA
<213> ORGANISM: Homo Sapiens

<400> SEQUENCE: 2
uugcugugug aggcagaacc ugcgggggca ggggcgggcu gguucccugg ccagccauug    60
gcagaguccg caggcuaggg cugucaauca ugcuggccgg cguggccccg ccuccgccgg   120 cgcgccccg ccuccgccgg cgcacgucug ggacgcaagg cgccgugggg gcugccggga   180 cgggccaag auggacggcc gcucagguuc ugcuuuuacc ugcggcccag agccccauuc   240

```
auugccccgg ugcugagcgg cgccgcgagu cggcccgagg ccuccgggga cugccgugcc    300
gggcgggaga ccgccauggc gacccuggaa aagcugauga aggccuucga gucccucaag    360
uccuuccagc agcagcagca gcagcagcag cagcagcagc agcagcagca gcagcagcag    420
cagcagcagc aacagccgcc accgccgccg ccgccgccgc cgccuccuca gcuuccucag    480
ccgccgccgc aggcacagcc gcugcugccu cagccgcagc cgcccccgcc gccgccccg    540 ccgccacccg gcccggcugu ggcugaggag ccgcugcacc gaccgugagu uugggcccgc    600
ugcagcuccc uguc                                                      614

<210> SEQ ID NO 3
<211> LENGTH: 19
<212> TYPE: RNA
<213> ORGANISM: artificial sequence
<220> FEATURE:
<223> OTHER INFORMATION: first sequence targeting huntingtin (guide)

<400> SEQUENCE: 3
aaggacuuga gggacucga                                                  19

<210> SEQ ID NO 4
<211> LENGTH: 20
<212> TYPE: RNA
<213> ORGANISM: artificial sequence
<220> FEATURE:
<223> OTHER INFORMATION: first sequence targeting huntingtin (guide)

<400> SEQUENCE: 4
aaggacuuga gggacucgaa                                                 20

<210> SEQ ID NO 5
<211> LENGTH: 21
<212> TYPE: RNA
<213> ORGANISM: artificial sequence
<220> FEATURE:
<223> OTHER INFORMATION: first sequence targeting huntingtin (guide)

<400> SEQUENCE: 5
aaggacuuga gggacucgaa g                                               21

<210> SEQ ID NO 6
<211> LENGTH: 22
<212> TYPE: RNA
<213> ORGANISM: artificial sequence
<220> FEATURE:
<223> OTHER INFORMATION: first sequence targeting huntingtin (guide)

<400> SEQUENCE: 6
aaggacuuga gggacucgaa gg                                              22

<210> SEQ ID NO 7
<211> LENGTH: 23
<212> TYPE: RNA
<213> ORGANISM: artificial sequence
<220> FEATURE:
<223> OTHER INFORMATION: first sequence targeting huntingtin (guide)

<400> SEQUENCE: 7
aaggacuuga gggacucgaa ggc                                             23

<210> SEQ ID NO 8
<211> LENGTH: 19
<212> TYPE: RNA
```

```
<213> ORGANISM: artificial sequence
<220> FEATURE:
<223> OTHER INFORMATION: second sequence (passenger)

<400> SEQUENCE: 8
ucgagucccu caaguccuu                                                    19

<210> SEQ ID NO 9
<211> LENGTH: 20
<212> TYPE: RNA
<213> ORGANISM: artificial sequence
<220> FEATURE:
<223> OTHER INFORMATION: second sequence (passenger)

<400> SEQUENCE: 9
uucgaguccc ucaaguccuu                                                   20

<210> SEQ ID NO 10
<211> LENGTH: 21
<212> TYPE: RNA
<213> ORGANISM: artificial sequence
<220> FEATURE:
<223> OTHER INFORMATION: second sequence (passenger)

<400> SEQUENCE: 10
cuucgagucc ucaaguccu u                                                  21

<210> SEQ ID NO 11
<211> LENGTH: 22
<212> TYPE: RNA
<213> ORGANISM: artificial sequence
<220> FEATURE:
<223> OTHER INFORMATION: second sequence (passenger)

<400> SEQUENCE: 11
ccuucgaguc ccucaagucc uu                                                22

<210> SEQ ID NO 12
<211> LENGTH: 23
<212> TYPE: RNA
<213> ORGANISM: artificial sequence
<220> FEATURE:
<223> OTHER INFORMATION: second sequence (passenger)

<400> SEQUENCE: 12
gccuucgagu cccucaaguc cuu                                               23

<210> SEQ ID NO 13
<211> LENGTH: 19
<212> TYPE: RNA
<213> ORGANISM: artificial sequence
<220> FEATURE:
<223> OTHER INFORMATION: second sequence (passenger)

<400> SEQUENCE: 13
cuucgagucu caaguccuu                                                    19

<210> SEQ ID NO 14
<211> LENGTH: 19
<212> TYPE: RNA
<213> ORGANISM: artificial sequence
<220> FEATURE:
<223> OTHER INFORMATION: second sequence (passenger)

<400> SEQUENCE: 14
acgagucccu caagaccuc                                                    19
```

<210> SEQ ID NO 15
<211> LENGTH: 72
<212> TYPE: RNA
<213> ORGANISM: artificial sequence
<220> FEATURE:
<223> OTHER INFORMATION: pre-miR451a scaffold

<400> SEQUENCE: 15

```
cuugggaaug gcaaggaagg acuugaggga cucgaagacg aguccucaa guccucucuu    60 gcuauaccca ga                                                       72
```

<210> SEQ ID NO 16
<211> LENGTH: 69
<212> TYPE: RNA
<213> ORGANISM: artificial sequence
<220> FEATURE:
<223> OTHER INFORMATION: pre-miR155 scaffold

<400> SEQUENCE: 16

```
ugcugaagga cuugagggac ucgaagguuu uggccacuga cugaccuucg agucucaagu    60
ccuucagga                                                           69
```

<210> SEQ ID NO 17
<211> LENGTH: 1989
<212> TYPE: DNA
<213> ORGANISM: artificial sequence
<220> FEATURE:
<223> OTHER INFORMATION: pVD-CMV-miH12-155

<400> SEQUENCE: 17

```
gttgacattg attattgact agttattaat agtaatcaat tacggggtca ttagttcata    60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
atcaagtgta tcatatgcca agtacgcccc ctattgacgt caatgacggt aaatggcccg   300
cctggcatta tgcccagtac atgaccttat ggactttcc tacttggcag tacatctacg   360
tattagtcat cgctattacc atggtgatgc ggttttggca gtacatcaat gggcgtggat   420
agcggtttga ctcacgggga tttccaagtc tccaccccat tgacgtcaat gggagtttgt   480
tttggcacca aaatcaacgg gactttccaa aatgtcgtaa caactccgcc ccattgacgc   540
aaatgggcgg taggcgtgta cggtgggagg tctataaag cagagctctc tggctaacta   600
gagaacccac tgcttactgg cttatcgaaa ttaatacgac tcactatagg gagtcccaag   660
ctggctagtt aagctatcaa caagtttgta caaaaaagca ggctttaaaa ccatggtgag   720
caagggcgag gagctgttca ccggggtggt gcccatcctg gtcgagctgg acggcgacgt   780
aaacggccac aagttcagcg tgtccggcga gggcgagggc gatgccacct acggcaagct   840
gaccctgaag ttcatctgca ccaccggcaa gctgcccgtg ccctggccca cctcgtgac   900 caccttcacc tacggcgtgc agtgcttcgc ccgctacccc gaccacatga agcagcacga   960
cttcttcaag tccgccatgc ccgaaggcta cgtccaggag cgcaccatct tcttcaagga  1020
cgacggcaac tacaagaccc gcgccgaggt gaagttcgag ggcgacaccc tggtgaaccg  1080
catcgagctg aagggcatcg acttcaagga ggacggcaac atcctggggc acaagctgga  1140
gtacaactac aacagccaca aggtctatat caccgccgac aagcagaaga acggcatcaa  1200
```

| | |
|---|---|
| ggtgaacttc aagacccgcc acaacatcga ggacggcagc gtgcagctcg ccgaccacta | 1260 |
| ccagcagaac accccatcg gcgacggccc cgtgctgctg cccgacaacc actacctgag | 1320 |
| cacccagtcc gccctgagca agaccccaa cgagaagcgc gatcacatgg tcctgctgga | 1380 |
| gttcgtgacc gccgccggga tcactctcgg catggacgag ctgtacaagt aagctaagca | 1440 |
| cttcgtggcc gtcgatcgtt taaagggagg tagtgagtcg accagtggat cctggaggct | 1500 |
| tgctgaaggc tgtatgctga aggacttgag ggactcgaag gttttggcca ctgactgacc | 1560 |
| ttcgagtctc aagtccttca ggacacaagg cctgttacta gcactcacat ggaacaaatg | 1620 |
| gcccagatct ggccgcactc gagatatcta gacccagctt tcttgtacaa agtggttgat | 1680 |
| ctagagggcc cgcggttcgc tgatggggga ggctaactga aacacggaag gagacaatac | 1740 |
| cggaaggaac ccgcgctatg acggcaataa aagacagaa taaaacgcac gggtgttggg | 1800 |
| tcgtttgttc ataaacgcgg ggttcggtcc cagggctggc actctgtcga taccccaccg | 1860 |
| tgacccatt ggggccaata cgcccgcgtt tcttccttt ccccacccca cccccaagt | 1920 |
| tcgggtgaag gcccagggct cgcagccaac gtcggggcgg caggccctgc catagcatcc | 1980 |
| cctatagtg | 1989 |

<210> SEQ ID NO 18
<211> LENGTH: 2444
<212> TYPE: DNA
<213> ORGANISM: artificial sequence
<220> FEATURE:
<223> OTHER INFORMATION: pVD-CAG-miH12-451

<400> SEQUENCE: 18

| | |
|---|---|
| cagtcacgac gttgtaaaac gacggccagt gaattcgccc ttaattcggt accctagtta | 60 |
| ttaatagtaa tcaattacgg ggtcattagt tcatagccca tatatggagt tccgcgttac | 120 |
| ataacttacg gtaaatggcc cgcctggctg accgcccaac gacccccgcc cattgacgtc | 180 |
| aataatgacg tatgttccca tagtaacgcc aatagggact ttccattgac gtcaatgggt | 240 |
| ggactattta cggtaaactg cccacttggc agtacatcaa gtgtatcata tgccaagtac | 300 |
| gccccctatt gacgtcaatg acggtaaatg gcccgcctgg cattatgccc agtacatgac | 360 |
| cttatgggac tttcctactt ggcagtacat ctacgtatta gtcatcgcta ttaccatggt | 420 |
| cgaggtgagc cccacgttct gcttcactct ccccatctcc cccccctccc cacccccaat | 480 |
| tttgtattta tttatttttt aattattttg tgcagcgatg ggggcggggg ggggggggg | 540 |
| gcgcgcgcca ggcggggcgg ggcggggcga ggggcgggc ggggcgaggc ggagaggtgc | 600 |
| ggcggcagcc aatcagagcg gcgcgctccg aaagtttcct tttatggcga ggcggcggcg | 660 |
| gcggcggccc tataaaaagc gaagcgcgcg cgggcgggga gtcgctgcga cgctgccttc | 720 |
| gccccgtgcc ccgctccgcc gccgcctcgc gccgcccgcc ccggctctga ctgaccgcgt | 780 |
| tactcccaca gtgagcgggc gggacggccc ttctcctcc gggctgtaat tagcgcttgg | 840 |
| tttaatgacg gcttgtttct tttctgtggc tgcgtgaaag ccttgagggg ctccgggagg | 900 |
| gccctttgtg cgggggggag cggctcgggg ggtgcgtgcg tgtgtgtgtg cgtggggagc | 960 |
| gccgcgtgcg gcccgcgctg cccggcggct gtgagcgctg cggcgcggc gcgggctt | 1020 |
| gtgcgctccg cagtgtgcgc gaggggagcg cggccgggg cggtgcccg cggtgcgggg | 1080 |
| ggggctgcga ggggaacaaa ggctgcgtgc gggtgtgtg cgtgggggg tgagcaggg | 1140 |
| gtgtgggcgc ggcggtcggg ctgtaacccc ccctgcacc cccctcccg agttgctgag | 1200 |
| cacggcccgg cttcgggtgc ggggctccgt acggggcgtg gcgcggggct cgccgtgccg | 1260 |

```
ggcgggggt  ggcggcaggt  gggggtgccg  ggcggggcgg  ggccgcctcg  ggccggggag    1320
ggctcggggg  aggggcgcgg  cggccccggg  agcgccggcg  gctgtcgagg  cgcggcgcgc    1380
cgcagccatt  gccttttatg  gtaatcgtgc  gagagggcgc  agggacttcc  tttgtcccaa    1440
atctgtgcga  agccgaaatc  tgggaggcgc  cgccgcaccc  cctctagcgg  gcgcggggcg    1500
aagcggtgcg  gcgccggcag  gaaggaaatg  ggcggggagg  gccttcgtgc  gtcgccgcgc    1560
cgccgtcccc  ttctccctct  ccagcctcgg  ggctgtccgc  gggggacggg  ctgccttcgg    1620
gggggacggg  gcagggcggg  gttcggcttc  tggcgtgtga  ccggcggctc  tagagcctct    1680
gctaaccatg  ttcatgcctt  cttcttttc   ctacagctcc  tgggcaacgt  gctggttatt    1740
gtgctgtctc  atcattttgg  caaagaatta  agggcgaatt  cgagctcggt  acctcgcgaa    1800
tgcatctaga  tatcgcgct   atgcttcctg  tgccccagt   ggggccctgg  ctgggatttc    1860
atcatatact  gtaagtttgc  gatgagacac  tacagtatag  atgatgtact  agtccgggca    1920
cccccagctc  tggagcctga  caaggaggac  aggagagatg  ctgcaagccc  aagaagctct    1980
ctgctcagcc  tgtcacaacc  tactgactgc  cagggcactt  gggaatggca  aggaaggact    2040
tgagggactc  gaagacgagt  ccctcaagtc  ctctcttgct  atacccagaa  aacgtgccag    2100
gaagagaact  caggaccctg  aagcagacta  ctggaaggga  gactccagct  caaacaaggc    2160
aggggtgggg  gcgtgggatt  ggggtaggg   gagggaatag  atacatttc   tctttcctgt    2220 tgtaaagaaa  taaagataag  ccaggcacag  tggctcacgc  ctgtaatccc  accactttca    2280
gaggccaagg  cgctggatcc  agatctcgag  cggccgcccg  tggcatccct  gtgacccctc    2340
cccagtgcct  ctcctggccc  tggaagttgc  cactccagtg  cccaccagcc  ttgtcctaat    2400
aaaattaagt  tgcatcaaga  tcgacgggcc  cgtcgactgc  agag                      2444

<210> SEQ ID NO 19
<211> LENGTH: 1224
<212> TYPE: DNA
<213> ORGANISM: artificial sequence
<220> FEATURE:
<223> OTHER INFORMATION: pVD-PGK-miH12-451

<400> SEQUENCE: 19
gttgtaaaac  gacggccagt  gaattctacc  gggtagggga  ggcgcttttc  ccaaggcagt      60
ctggagcatg  cgctttagca  gccccgctgg  gcacttggcg  ctacacaagt  ggcctctggc     120
ctcgcacaca  ttccacatcc  accggtaggc  gccaaccggc  tccgttcttt  ggtggcccct     180
tcgcgccacc  ttctactcct  cccctagtca  ggaagttccc  ccccgccccg  cagctcgcgt     240
cgtgcaggac  gtgacaaatg  gaagtagcac  gtctcactag  tctcgtgcag  atggacagca     300
ccgctgagca  atggaagcgg  gtaggccttt  ggggcagcgg  ccaatagcag  ctttgctcct     360
tcgctttctg  ggctcagagg  ctgggaaggg  gtgggtccgg  gggcgggctc  agggcgggc     420 tcaggggcgg  ggcgggcgcc  cgaaggtcct  ccggaggccc  ggcattctgc  acgcttcaaa     480
agcgcacgtc  tgccgcgctg  ttctcctctt  cctcatctcc  gggcctttcg  acccggatcc     540
cccgggctgc  aggaattcga  gctcggtacc  tcgcgaatgc  atctagatat  cggcgctatg     600
cttcctgtgc  cccagtggg   gcctggctg   ggatttcatc  atatactgta  agtttgcgat     660
gagacactac  agtatagatg  atgtactagt  ccgggcaccc  ccagctctgg  agcctgacaa     720
ggaggacagg  agagatgctg  caagcccaag  aagctctctg  ctcagcctgt  cacaacctac     780
tgactgccag  ggcacttggg  aatggcaagg  aaggacttga  gggactcgaa  gacgagtccc     840
```

```
tcaagtcctc tcttgctata cccagaaaac gtgccaggaa gagaactcag gaccctgaag      900
cagactactg gaagggagac tccagctcaa acaaggcagg ggtggggggcg tgggattggg      960 ggtaggggag ggaatagata cattttctct ttcctgttgt aaagaaataa agataagcca     1020
ggcacagtgg ctcacgcctg taatcccacc actttcagag gccaaggcgc tggatccaga     1080
tctcgagcgg ccgcccgtgg catccctgtg acccctcccc agtgcctctc ctggccctgg     1140
aagttgccac tccagtgccc accagccttg tcctaataaa attaagttgc atcaagatcg     1200
acgggcccgt cgactgcaga ggcc                                            1224

<210> SEQ ID NO 20
<211> LENGTH: 272
<212> TYPE: RNA
<213> ORGANISM: artificial sequence
<220> FEATURE:
<223> OTHER INFORMATION: scaffold pri-miH12-155

<400> SEQUENCE: 20
gcuaagcacu ucguggccgu cgaucguuua aagggaggua gugagucgac cagguggaucc       60 uggaggcuug cugaaggcug uaugcugaag gacuugaggg acucgaaggu uuuggccacu      120
gacugaccuu cgagucucaa guccuucagg acacaaggcc uguuacuagc acucacaugg      180
aacaaauggc ccagaucugg ccgcacucga gauaucuaga cccagcuuuc uuguacaaag      240
ugguugaucu agagggcccg cgguucgcug au                                   272

<210> SEQ ID NO 21
<211> LENGTH: 605
<212> TYPE: RNA
<213> ORGANISM: artificial sequence
<220> FEATURE:
<223> OTHER INFORMATION: scaffold pri-miH12-451

<400> SEQUENCE: 21
gcuccugggc aacgugcugg uuauugugcu gucucaucau uuuggcaaag aauuaagggc       60
gaauucgagc ucgguaccuc gcgaaugcau cuagauaucg gcgcuaugcu uccugugccc      120
ccaguggggc ccuggcuggg auuucaucau auacuguaag uuugcgauga gacacuacag      180
uauagaugau guacuagucc gggcaccccc agcucuggag ccugacaagg aggacaggag      240
agaugcugca agcccaagaa gcucucugcu cagccuguca caaccuacug acugccaggg      300
cacuugggaa uggcaaggaa ggacuugagg gacucgaaga cgaguccuc aaguccucuc      360 uugcuauacc cagaaaacgu gccaggaaga gaacucagga cccugaagca gacuacugga      420
agggagacuc cagcucaaac aaggcagggg uggggcgug ggauuggggg uagggagggg       480
aauagauaca uuuucucuuu ccuguuguaa agaaauaaag auaagccagg cacaguggcu      540
cacgccugua aucccaccac uuucagaggc caaggcgcug gauccagauc ucgagcggcc      600
gcccg                                                                 605

<210> SEQ ID NO 22
<211> LENGTH: 819
<212> TYPE: RNA
<213> ORGANISM: artificial sequence
<220> FEATURE:
<223> OTHER INFORMATION: scaffold pri-miH12-451

<400> SEQUENCE: 22
agucucgugc agauggacag caccgcugag caauggaagc ggguaggccu uuggggcagc       60
ggccaauagc agcuuugcuc cuucgcuuuc ugggcucaga ggcugggaag ggugugggucc      120
```

```
gggggcgggc ucaggggcgg gcucagggcc ggggcgggcg cccgaagguc ucccggaggc      180
ccggcauucu gcacgcuuca aaagcgcacg ucugccgcgc uguucuccuc uuccucaucu      240
ccgggccuuu cgacccggau ccccccgggcu gcaggaauuc gagcucggua ccucgcgaau    300
gcaucuagau aucggcgcua ugcuuccugu gccccccagug gggcccuggc ugggauuuca    360
ucauauacug uaaguuugcg augagacacu acaguauaga ugauguacua guccgggcac     420
ccccagcucu ggagccugac aaggaggaca ggagagaugc ugcaagccca agaagcucuc      480
ugcucagccu gucacaaccu acugacugcc agggcacuug ggaauggcaa ggaaggacuu     540
gagggacucg aagacgaguc ccucaagucc ucucuugcua acccagaaaa acgugccagg      600
aagagaacuc aggacccuga agcagacuac uggaagggag acuccagcuc aaacaaggca     660 ggggugggg cgugggauug ggguaggggg agggaauaga uacauuuucu cuuccuguu       720 guaaagaaau aaagauaagc caggcacagu ggcucacgcc uguaauccca ccacuuucag     780
aggccaaggc gcuggaucca gaucucgagc ggccgcccg                            819

<210> SEQ ID NO 23
<211> LENGTH: 21
<212> TYPE: DNA
<213> ORGANISM: homo sapiens

<400> SEQUENCE: 23
tccaagatgg acggccgctc a                                                21

<210> SEQ ID NO 24
<211> LENGTH: 21
<212> TYPE: DNA
<213> ORGANISM: homo sapiens

<400> SEQUENCE: 24
ccaagatgga cggccgctca g                                                21

<210> SEQ ID NO 25
<211> LENGTH: 21
<212> TYPE: DNA
<213> ORGANISM: homo sapiens

<400> SEQUENCE: 25
agatggacgg ccgctcaggt t                                                21

<210> SEQ ID NO 26
<211> LENGTH: 21
<212> TYPE: DNA
<213> ORGANISM: homo sapiens

<400> SEQUENCE: 26
atggacggcc gctcaggttc t                                                21

<210> SEQ ID NO 27
<211> LENGTH: 21
<212> TYPE: DNA
<213> ORGANISM: homo sapiens

<400> SEQUENCE: 27
gacggccgct caggttctgc t                                                21

<210> SEQ ID NO 28
<211> LENGTH: 21
<212> TYPE: DNA
```

<213> ORGANISM: homo sapiens

<400> SEQUENCE: 28
cggccgctca ggttctgctt t                    21

<210> SEQ ID NO 29
<211> LENGTH: 21
<212> TYPE: DNA
<213> ORGANISM: homo sapiens

<400> SEQUENCE: 29
gtgctgagcg gcgccgcgag t                    21

<210> SEQ ID NO 30
<211> LENGTH: 21
<212> TYPE: DNA
<213> ORGANISM: homo sapiens

<400> SEQUENCE: 30
cgccgcgagt cggcccgagg c                    21

<210> SEQ ID NO 31
<211> LENGTH: 21
<212> TYPE: DNA
<213> ORGANISM: homo sapiens

<400> SEQUENCE: 31
accgccatgg cgaccctgga a                    21

<210> SEQ ID NO 32
<211> LENGTH: 21
<212> TYPE: DNA
<213> ORGANISM: homo sapiens

<400> SEQUENCE: 32
ccgccatggc gaccctggaa a                    21

<210> SEQ ID NO 33
<211> LENGTH: 21
<212> TYPE: DNA
<213> ORGANISM: homo sapiens

<400> SEQUENCE: 33
gaaggccttc gagtccctca a                    21

<210> SEQ ID NO 34
<211> LENGTH: 21
<212> TYPE: DNA
<213> ORGANISM: homo sapiens

<400> SEQUENCE: 34
cttcgagtcc ctcaagtcct t                    21

<210> SEQ ID NO 35
<211> LENGTH: 21
<212> TYPE: DNA
<213> ORGANISM: homo sapiens

<400> SEQUENCE: 35
ccgccgccgc ctcctcagct t                    21

<210> SEQ ID NO 36
<211> LENGTH: 21

<212> TYPE: DNA
<213> ORGANISM: homo sapiens

<400> SEQUENCE: 36
gccgcctcct cagcttcctc a                                              21

<210> SEQ ID NO 37
<211> LENGTH: 21
<212> TYPE: DNA
<213> ORGANISM: homo sapiens

<400> SEQUENCE: 37
tcagccgccg ccgcaggcac a                                              21

<210> SEQ ID NO 38
<211> LENGTH: 21
<212> TYPE: DNA
<213> ORGANISM: homo sapiens

<400> SEQUENCE: 38
gccgcaggca cagccgctgc t                                              21

<210> SEQ ID NO 39
<211> LENGTH: 21
<212> TYPE: DNA
<213> ORGANISM: homo sapiens

<400> SEQUENCE: 39
ggcacagccg ctgctgcctc a                                              21

<210> SEQ ID NO 40
<211> LENGTH: 21
<212> TYPE: DNA
<213> ORGANISM: homo sapiens

<400> SEQUENCE: 40
gccgctgctg cctcagccgc a                                              21

<210> SEQ ID NO 41
<211> LENGTH: 21
<212> TYPE: DNA
<213> ORGANISM: homo sapiens

<400> SEQUENCE: 41
cggcccggct gtggctgagg a                                              21

<210> SEQ ID NO 42
<211> LENGTH: 21
<212> TYPE: DNA
<213> ORGANISM: homo sapiens

<400> SEQUENCE: 42
ctgtggctga ggagccgctg c                                              21

<210> SEQ ID NO 43
<211> LENGTH: 21
<212> TYPE: DNA
<213> ORGANISM: homo sapiens

<400> SEQUENCE: 43
tgtggctgag gagccgctgc a                                              21

<210> SEQ ID NO 44

```
<211> LENGTH: 69
<212> TYPE: RNA
<213> ORGANISM: artificial sequence
<220> FEATURE:
<223> OTHER INFORMATION: miH12_155 scaffold sequence figure 2A

<400> SEQUENCE: 44
ugcugaagga cuugagggac ucgaagguuu uggccacuga cugaccuucg agucucaagu    60
ccuucagga                                                           69

<210> SEQ ID NO 45
<211> LENGTH: 72
<212> TYPE: RNA
<213> ORGANISM: artificial sequence
<220> FEATURE:
<223> OTHER INFORMATION: miH12_451a scaffold sequence figure 2A

<400> SEQUENCE: 45
cuugggaaug gcaaggaagg acuugaggga cucgaagacg agucccucaa guccucucuu    60
gcauacccca ga                                                       72

<210> SEQ ID NO 46
<211> LENGTH: 21
<212> TYPE: RNA
<213> ORGANISM: Homo sapiens

<400> SEQUENCE: 46
ggccucgagu cccucaaguc c                                             21

<210> SEQ ID NO 47
<211> LENGTH: 21
<212> TYPE: RNA
<213> ORGANISM: homo sapiens

<400> SEQUENCE: 47
ggccuucgag ucccucaagu c                                             21

<210> SEQ ID NO 48
<211> LENGTH: 21
<212> TYPE: RNA
<213> ORGANISM: homo sapiens

<400> SEQUENCE: 48
aggccuucga gucccucaag u                                             21

<210> SEQ ID NO 49
<211> LENGTH: 21
<212> TYPE: RNA
<213> ORGANISM: homo sapiens

<400> SEQUENCE: 49
augaaggccu ucgagucccu c                                             21

<210> SEQ ID NO 50
<211> LENGTH: 19
<212> TYPE: RNA
<213> ORGANISM: homo sapiens

<400> SEQUENCE: 50
gccuucgagu cccucaagu                                                19

<210> SEQ ID NO 51
<211> LENGTH: 18
```

```
<212> TYPE: RNA
<213> ORGANISM: homo sapiens

<400> SEQUENCE: 51
ccuucgaguc ccucaagu                                                 18
```